(12) United States Patent
Jensen

(10) Patent No.: US 7,537,596 B2
(45) Date of Patent: May 26, 2009

(54) BONE PLATES WITH INTRAOPERATIVELY TAPPED APERTURES

(75) Inventor: David G. Jensen, Troutdale, OR (US)

(73) Assignee: Acumed LLC, Hillsboro, OR (US)

( * ) Notice: Subject to any disclaimer, the term of this patent is extended or adjusted under 35 U.S.C. 154(b) by 398 days.

(21) Appl. No.: 10/873,522

(22) Filed: Jun. 21, 2004

(65) Prior Publication Data

US 2004/0260291 A1    Dec. 23, 2004

Related U.S. Application Data

(60) Provisional application No. 60/480,529, filed on Jun. 20, 2003.

(51) Int. Cl.
*A61B 17/56* (2006.01)
(52) U.S. Cl. .......................... 606/69; 606/73
(58) Field of Classification Search .................. 606/61, 606/69, 70, 71, 80; 408/222; 470/198
See application file for complete search history.

(56) References Cited

U.S. PATENT DOCUMENTS

| | | | |
|---|---|---|---|
| 820,503 A | 5/1906 | Krengel et al. | |
| 869,697 A | 10/1907 | Eilhauer et al. | |
| 1,105,105 A | 7/1914 | Sherman | |
| 1,345,425 A * | 7/1920 | Wells | 408/219 |
| 1,789,060 A | 1/1931 | Weisenbach | |
| 1,889,239 A | 11/1932 | Crowley | |
| 2,406,832 A | 9/1946 | Hardinge | |
| 2,443,363 A | 6/1948 | Townsend et al. | |
| 2,489,870 A | 11/1949 | Dzus | |
| 2,494,229 A | 1/1950 | Collison | |
| 2,500,370 A | 3/1950 | McKibbin | |
| 2,526,959 A | 10/1950 | Lorenzo | |
| 2,580,821 A | 1/1952 | Nicola | |
| 2,583,896 A | 1/1952 | Siebrandt | |
| 2,737,835 A | 3/1956 | Herz | |
| 3,025,853 A | 3/1962 | Mason | |
| 3,072,423 A | 1/1963 | Charlton | |

(Continued)

FOREIGN PATENT DOCUMENTS

AU         89750/91        2/1992

(Continued)

OTHER PUBLICATIONS

McBride S.M.O. Stainless Steel Bone Plates brochure, DePuy, Inc., 1943.
Bone Plates brochure, Vitallium, Mar. 1948.
Dupont Distal Humeral Plates brochure, Howmedica Inc., 1990.
The Arnett-TMP* Titanium Miniplating System brochure, Techmedica, Inc., 1989.

(Continued)

*Primary Examiner*—Eduardo C. Robert
*Assistant Examiner*—Annette Reimers
(74) *Attorney, Agent, or Firm*—Kolisch Hartwell, P.C.

(57) ABSTRACT

Method of tapping a bone plate intraoperatively. A bone plate having an aperture may be selected, and the bone plate may be placed on a bone. A thread may be formed in the aperture using a tap device with the bone plate disposed on the bone. A hole may be formed in the bone, with the hole in alignment with the aperture. The hole may be widened adjacent the aperture to create a counterbore in the bone. A fastener may be advanced into threaded engagement with the thread after removal of the tap device from the aperture.

18 Claims, 6 Drawing Sheets

U.S. PATENT DOCUMENTS

| | | |
|---|---|---|
| 3,171,518 A | 3/1965 | Bergmann |
| 3,244,170 A | 4/1966 | McElvenny |
| 3,346,894 A * | 10/1967 | Lemelson .................... 408/12 |
| 3,386,437 A | 6/1968 | Treace |
| 3,488,779 A | 1/1970 | Christensen |
| 3,489,143 A | 1/1970 | Halloran |
| 3,593,709 A | 7/1971 | Halloran |
| 3,604,414 A | 9/1971 | Borges |
| 3,716,050 A | 2/1973 | Johnston |
| 3,741,205 A | 6/1973 | Markolf et al. |
| 3,842,825 A | 10/1974 | Wagner |
| 3,866,458 A | 2/1975 | Wagner |
| 3,867,932 A * | 2/1975 | Huene ........................ 606/80 |
| 3,900,025 A | 8/1975 | Barnes, Jr. |
| 3,901,064 A | 8/1975 | Jacobson |
| 3,939,497 A | 2/1976 | Heimke et al. |
| 3,965,720 A | 6/1976 | Goodwin et al. |
| 4,119,092 A | 10/1978 | Gil |
| 4,187,840 A | 2/1980 | Watanabe |
| 4,187,841 A | 2/1980 | Knutson |
| 4,201,215 A | 5/1980 | Crossett et al. |
| 4,364,382 A | 12/1982 | Mennen |
| 4,388,921 A | 6/1983 | Sutter et al. |
| 4,408,601 A | 10/1983 | Wenk |
| RE31,628 E | 7/1984 | Allgower et al. |
| 4,457,307 A | 7/1984 | Stillwell |
| 4,484,570 A | 11/1984 | Sutter et al. |
| 4,493,317 A | 1/1985 | Klaue |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,651,724 A | 3/1987 | Berentey et al. |
| 4,683,878 A | 8/1987 | Carter |
| 4,703,751 A | 11/1987 | Pohl |
| 4,705,031 A | 11/1987 | Wolter |
| 4,718,413 A | 1/1988 | Johnson |
| 4,730,608 A | 3/1988 | Schlein |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |
| 4,867,144 A | 9/1989 | Karas et al. |
| 4,892,093 A | 1/1990 | Zarnowski et al. |
| 4,893,619 A | 1/1990 | Dale et al. |
| 4,903,691 A | 2/1990 | Heinl |
| 4,905,679 A | 3/1990 | Morgan |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karas et al. |
| 4,966,599 A | 10/1990 | Pollock |
| 4,973,332 A | 11/1990 | Kummer |
| 4,988,350 A | 1/1991 | Herzberg |
| 5,002,544 A | 3/1991 | Klaue et al. |
| 5,006,120 A | 4/1991 | Carter |
| 5,013,315 A | 5/1991 | Barrows |
| 5,015,248 A | 5/1991 | Burstein et al. |
| 5,021,056 A | 6/1991 | Hofmann et al. |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,129,899 A | 7/1992 | Small et al. |
| 5,133,718 A | 7/1992 | Mao |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,737 A | 4/1993 | Leibinger et al. |
| 5,234,431 A | 8/1993 | Keller |
| 5,254,119 A | 10/1993 | Schreiber |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,364,398 A | 11/1994 | Chapman et al. |
| 5,364,399 A | 11/1994 | Lowery et al. |
| 5,380,327 A | 1/1995 | Eggers et al. |
| 5,413,577 A | 5/1995 | Pollock |
| 5,413,579 A | 5/1995 | Du Toit |
| 5,423,826 A | 6/1995 | Coates et al. |
| 5,443,516 A | 8/1995 | Albrektsson et al. |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Proctor et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,607,426 A | 3/1997 | Ralph et al. |
| 5,643,261 A | 7/1997 | Schafer et al. |
| 5,643,265 A | 7/1997 | Errico et al. |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,667 A | 10/1997 | Hausman |
| 5,681,313 A | 10/1997 | Diez |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |

| | | |
|---|---|---|
| 5,810,824 A | 9/1998 | Chan |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,902,304 A | 5/1999 | Walker et al. |
| 5,904,683 A | 5/1999 | Pohndorf et al. |
| 5,916,216 A | 6/1999 | DeSatnick et al. |
| 5,919,195 A | 7/1999 | Wilson et al. |
| 5,928,234 A | 7/1999 | Manspeizer |
| 5,931,839 A | 8/1999 | Medoff |
| 5,938,664 A | 8/1999 | Winquist et al. |
| 5,941,878 A | 8/1999 | Medoff |
| 5,951,557 A | 9/1999 | Luter |
| 5,954,722 A | 9/1999 | Bono |
| 5,964,763 A | 10/1999 | Incavo et al. |
| 5,968,046 A | 10/1999 | Castleman |
| 5,968,047 A | 10/1999 | Reed |
| 5,973,223 A | 10/1999 | Tellman et al. |
| 6,001,099 A | 12/1999 | Huebner |
| 6,004,323 A | 12/1999 | Park et al. |
| 6,004,353 A | 12/1999 | Masini |
| 6,007,535 A | 12/1999 | Rayhack et al. |
| 6,022,350 A | 2/2000 | Ganem |
| 6,027,504 A | 2/2000 | McGuire |
| 6,053,915 A | 4/2000 | Bruchmann |
| 6,077,266 A | 6/2000 | Medoff |
| 6,077,271 A | 6/2000 | Huebner et al. |
| 6,093,188 A | 7/2000 | Murray |
| 6,096,040 A | 8/2000 | Esser |
| 6,113,603 A | 9/2000 | Medoff |
| 6,117,160 A | 9/2000 | Bonutti |
| 6,123,709 A | 9/2000 | Jones |
| 6,129,728 A | 10/2000 | Schumacher et al. |
| 6,129,730 A | 10/2000 | Bono et al. |
| 6,139,548 A | 10/2000 | Errico |
| 6,152,927 A | 11/2000 | Farris et al. |
| 6,159,213 A | 12/2000 | Rogozinski |
| 6,179,839 B1 | 1/2001 | Weiss et al. |
| 6,183,475 B1 | 2/2001 | Lester et al. |
| 6,193,721 B1 | 2/2001 | Michelson |
| 6,197,028 B1 | 3/2001 | Ray et al. |
| 6,221,073 B1 | 4/2001 | Weiss et al. |
| 6,224,602 B1 | 5/2001 | Hayes |
| 6,228,087 B1 | 5/2001 | Fenaroli et al. |
| 6,235,033 B1 | 5/2001 | Brace et al. |
| 6,235,034 B1 | 5/2001 | Bray |
| 6,238,396 B1 | 5/2001 | Lombardo |
| 6,258,092 B1 | 7/2001 | Dall |
| 6,261,291 B1 | 7/2001 | Talaber et al. |
| 6,273,889 B1 | 8/2001 | Richelsoph |
| 6,283,969 B1 | 9/2001 | Grusin et al. |
| 6,290,703 B1 | 9/2001 | Ganem |
| 6,302,883 B1 | 10/2001 | Bono |
| 6,302,884 B1 | 10/2001 | Wellisz et al. |
| 6,302,887 B1 | 10/2001 | Spranza et al. |
| 6,306,136 B1 | 10/2001 | Baccelli |
| 6,312,431 B1 | 11/2001 | Asfora |
| 6,315,779 B1 | 11/2001 | Morrison et al. |
| 6,322,562 B1 * | 11/2001 | Wolter .................. 606/69 |
| 6,325,803 B1 | 12/2001 | Schumacher et al. |
| 6,331,179 B1 | 12/2001 | Freid et al. |
| 6,336,927 B2 | 1/2002 | Rogozinski |
| 6,338,734 B1 | 1/2002 | Burke et al. |
| 6,342,055 B1 | 1/2002 | Eisermann et al. |
| 6,342,075 B1 | 1/2002 | MacArthur |
| 6,355,036 B1 | 3/2002 | Nakajima |
| 6,355,042 B2 | 3/2002 | Winquist |
| 6,358,250 B1 | 3/2002 | Orbay |
| 6,364,881 B1 | 4/2002 | Apgar et al. |
| 6,364,882 B1 | 4/2002 | Orbay |
| 6,364,883 B1 | 4/2002 | Santilli |
| 6,379,354 B1 | 4/2002 | Rogozinski |
| 6,379,364 B1 | 4/2002 | Brace et al. |
| 6,402,756 B1 | 6/2002 | Ralph et al. |
| 6,413,259 B1 | 7/2002 | Lyons et al. |
| 6,428,542 B1 | 8/2002 | Michelson |
| 6,436,103 B1 | 8/2002 | Suddaby |
| 6,440,135 B2 | 8/2002 | Orbay et al. |
| 6,454,769 B2 | 9/2002 | Wagner et al. |
| 6,454,770 B2 | 9/2002 | Klaue |
| 6,458,133 B1 | 10/2002 | Lin |
| 6,503,250 B2 | 1/2003 | Paul |
| 6,508,819 B1 | 1/2003 | Orbay |
| 6,514,274 B1 | 2/2003 | Boucher et al. |
| 6,520,965 B2 | 2/2003 | Chervitz et al. |
| 6,527,775 B1 | 3/2003 | Warburton |
| 6,533,789 B1 | 3/2003 | Hall, IV et al. |
| 6,547,790 B2 | 4/2003 | Harkey et al. |
| 6,565,570 B2 | 5/2003 | Sterett et al. |
| 6,592,578 B2 | 7/2003 | Henniges et al. |
| 6,595,993 B2 | 7/2003 | Donno et al. |
| 6,602,255 B1 | 8/2003 | Campbell et al. |
| 6,623,486 B1 | 9/2003 | Weaver et al. |
| 6,623,487 B1 | 9/2003 | Goshert |
| 6,682,531 B2 | 1/2004 | Winquist et al. |
| 6,682,533 B1 | 1/2004 | Dinsdale et al. |
| 6,689,139 B2 | 2/2004 | Horn |
| 6,695,846 B2 | 2/2004 | Richelsoph et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,730,091 B1 | 5/2004 | Pfefferle et al. |
| 6,736,819 B2 | 5/2004 | Tipirneni |
| 6,767,351 B2 | 7/2004 | Orbay et al. |
| 6,793,658 B2 | 9/2004 | LeHuec et al. |
| 6,821,278 B2 | 11/2004 | Frigg et al. |
| 6,858,031 B2 | 2/2005 | Morrison et al. |
| 6,866,665 B2 | 3/2005 | Orbay |
| 6,893,444 B2 | 5/2005 | Orbay |
| 6,955,677 B2 | 10/2005 | Dahners |
| 6,974,461 B1 | 12/2005 | Wolter |
| 2001/0011172 A1 | 8/2001 | Orbay et al. |
| 2002/0004660 A1 | 1/2002 | Henniges et al. |
| 2002/0032446 A1 | 3/2002 | Orbay |
| 2002/0055741 A1 | 5/2002 | Schlapfer et al. |
| 2002/0128654 A1 | 9/2002 | Steger et al. |
| 2002/0143336 A1 | 10/2002 | Hearn |
| 2002/0143338 A1 | 10/2002 | Orbay et al. |
| 2002/0147453 A1 | 10/2002 | Gambale |
| 2002/0151899 A1 | 10/2002 | Bailey et al. |
| 2002/0156474 A1 | 10/2002 | Wack et al. |
| 2002/0173794 A1 | 11/2002 | Happonen et al. |
| 2002/0183752 A1 | 12/2002 | Steiner et al. |
| 2003/0018337 A1 | 1/2003 | Davis |
| 2003/0040748 A1 | 2/2003 | Aikins et al. |
| 2003/0055429 A1 | 3/2003 | Ip et al. |
| 2003/0105461 A1 | 6/2003 | Putnam |
| 2003/0149434 A1 | 8/2003 | Paul |
| 2003/0153918 A1 | 8/2003 | Putnam et al. |
| 2003/0233093 A1 | 12/2003 | Moles et al. |
| 2004/0073218 A1 | 4/2004 | Dahners |
| 2004/0102775 A1 | 5/2004 | Huebner |
| 2004/0102776 A1 | 5/2004 | Huebner |
| 2004/0102777 A1 | 5/2004 | Huebner |
| 2004/0102778 A1 | 5/2004 | Huebner et al. |
| 2004/0116930 A1 | 6/2004 | O'Driscoll et al. |
| 2004/0127901 A1 | 7/2004 | Huebner et al. |
| 2004/0127903 A1 | 7/2004 | Schlapfer et al. |
| 2004/0153073 A1 | 8/2004 | Orbay |
| 2004/0193164 A1 | 9/2004 | Orbay |
| 2004/0193165 A1 | 9/2004 | Orbay |
| 2004/0220566 A1 | 11/2004 | Bray |
| 2004/0260292 A1 | 12/2004 | Orbay et al. |

| | | | |
|---|---|---|---|
| 2004/0260293 A1 | 12/2004 | Orbay et al. | |
| 2004/0260294 A1 | 12/2004 | Orbay et al. | |
| 2004/0260295 A1 | 12/2004 | Orbay et al. | |
| 2005/0015089 A1 | 1/2005 | Young et al. | |
| 2005/0065520 A1 | 3/2005 | Orbay | |
| 2005/0065522 A1 | 3/2005 | Orbay | |
| 2005/0065523 A1 | 3/2005 | Orbay | |
| 2005/0065524 A1 | 3/2005 | Orbay | |
| 2005/0065528 A1 | 3/2005 | Orbay | |
| 2005/0085818 A1 | 4/2005 | Huebner | |
| 2005/0085819 A1 | 4/2005 | Ellis et al. | |
| 2005/0131413 A1 | 6/2005 | O'Driscoll et al. | |
| 2005/0159747 A1 | 7/2005 | Orbay | |
| 2005/0165395 A1 | 7/2005 | Orbay et al. | |
| 2005/0165400 A1 | 7/2005 | Fernandez | |
| 2005/0171544 A1 | 8/2005 | Falkner | |
| 2005/0182405 A1 | 8/2005 | Orbay et al. | |
| 2005/0182406 A1 | 8/2005 | Orbay et al. | |
| 2005/0187551 A1 | 8/2005 | Orbay et al. | |
| 2005/0192578 A1 | 9/2005 | Horst | |
| 2005/0234458 A1 | 10/2005 | Huebner | |

FOREIGN PATENT DOCUMENTS

| | | |
|---|---|---|
| CH | 474 344 | 8/1969 |
| CH | 611 147 | 5/1979 |
| CH | 613 617 | 10/1979 |
| DE | 2515430 | 11/1975 |
| DE | 26 21 122 | 11/1977 |
| DE | 26 21 123 | 11/1977 |
| DE | 26 21 124 | 11/1977 |
| DE | 26 21 125 | 11/1977 |
| DE | 26 25 529 | 12/1977 |
| DE | 27 33 428 | 2/1979 |
| DE | 28 32 555 | 2/1980 |
| DE | 29 47 839 | 7/1981 |
| DE | 29 47 885 | 7/1981 |
| DE | 4201531 | 7/1993 |
| DE | 4343117 | 6/1995 |
| DE | 196 29 011 | 1/1998 |
| DE | 198 58 889 | 6/2000 |
| DE | 199 62 317 | 3/2001 |
| DE | 103 09 090 | 9/2004 |
| EP | 0 053 999 | 6/1982 |
| EP | 0 242 842 | 10/1987 |
| EP | 0 410 309 | 1/1991 |
| EP | 0415837 A2 | 3/1991 |
| EP | 0471418 A1 | 2/1992 |
| EP | 0362049 B1 | 5/1992 |
| EP | 1 143 867 | 10/2001 |
| EP | 1 211 993 | 6/2002 |
| EP | 1 211 994 | 6/2002 |
| EP | 1 250 892 A2 | 9/2003 |
| EP | 1 250 892 A3 | 9/2003 |
| FR | 742.618 | 3/1933 |
| FR | 2 254 298 | 7/1975 |
| FR | 2367479 | 5/1978 |
| FR | 2405705 | 5/1979 |
| FR | 2405706 | 5/1979 |
| FR | 2406429 | 5/1979 |
| FR | 2472373 | 7/1981 |
| FR | 2674118 | 9/1992 |
| GB | 2245498 | 1/1992 |
| GB | 2 406 056 A | 3/2005 |
| GB | 2 419 096 | 4/2006 |
| SU | 610518 | 6/1978 |
| SU | 718097 | 2/1980 |
| SU | 862937 | 9/1981 |
| SU | 897233 | 1/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 A | 2/1992 |
| SU | 1734715 A1 | 5/1992 |
| WO | WO82/01645 | 5/1982 |
| WO | WO87/02572 | 5/1987 |
| WO | WO88/03781 | 6/1988 |
| WO | WO96/29948 | 10/1996 |
| WO | WO 97/47251 | 12/1997 |
| WO | WO 00/36984 | 6/2000 |
| WO | WO01/21083 A1 | 3/2001 |
| WO | WO01/62136 A3 | 8/2001 |
| WO | WO 03/105712 A2 | 12/2003 |
| WO | WO 2004/112587 | 12/2004 |
| WO | WO 2006/007965 | 1/2006 |

OTHER PUBLICATIONS

Techmedica Bioengineers Keep Tabs on Your Needs brochure, Techmedica, Inc., 1991.

A Comparison if Unicortical and Biocortical End Screw Attachment of Fracture Fixation Plates, Beaupre et al., *Journal of Orthopaedic Trauma*, vol. 6, No. 3, pp. 294-300, 1992.

Ace 4.5/5.0 mm Titanium Cannulated Screw and Reconstruction Plate System surgical technique brochure, Ace Medical Company, 1992.

Ace 4.5/5.0 mm Titanium Cannulated Screw and Reconstruction Plate System simplified fracture frixation brochure, Ace Medical Company, 1992.

Ace Titanium 3.5/4.0 mm Screw and Plate System with the Ace 3.5 mm Universal Ribbon CT/MRI compatible fixation brochure, Ace Medical Company, 1992.

Treatment of Three- and Four-Part Fractures of the Proximal Humerus with a Modified Cloverleaf Plate, Esser, *Journal of Orthopaedic Trauma*, vol. 8, No. 1, pp. 15-22, 1994.

Ace Symmetry Titanium Upper Extremity Plates surgical technique brochure, Ace Medical Company, 1996.

The Ace Symmetry Titanium Upper Extremity Plates new product release brochure, Ace Medical Company, 1996.

Small Titanium Plates overview page, Synthes, p. 2a-33, Mar. 1997.

Congruent Distal Radius Plate System description, Acumed, Inc., Mar. 4, 1998.

Salvage of Tibial Pilon Fractures Using Fusion of the Ankle with a 90° Cannulated Blade Plate: A Preliminary Report, Morgan et al., *Foot & Ankle International*, vol. 20, No. 6, pp. 375-378, Jun. 1999.

*Scaphoid Protocols Using the Acutrak® Bone Screw System* brochure, Toby, published by Acumed, Inc., Dec. 7, 1999.

Single Unit Osteosynthesis brochure, Surfix Technologies, Sep. 2000.

Supracondylar Cable Plate brochure, Biomet Orthopedics, Inc., 2000.

Principle-Based Internal Fixation of Distal Humerus Fractures, Sanchez-Sotelo et al., *Techniques in Hand & Upper Extremity Surgery*, vol. 5, No. 4, pp. 179-187, Dec. 2001.

Congruent Plate System—The Mayo Clinic Congruent Elbow Plates brochure, Acumed, Inc., May 7, 2002.

Modular Hand System brochure, Acumed, Inc., Aug. 2002.

Modular Hand System brochure, Acumed, Inc., Sep. 2002.

Periarticular Plating System brochure, Zimmer, Inc., 2002.

Jplate Diaphysis Plates for Japanese brochure, Mizuho Co., Ltd., 2002.

An Axially Mobile Plate for Fracture Fixation, Abel et al., *Internal Fixation in Osteoporotic Bone*, pp. 279-283, 2002.

The Use of Interlocked 'Customised' Blade Plates in the Treatment of Metaphyseal Fractures in Patients with Poor Bone Stock, Palmer et al., *Injury, Int. J. Care Injured*, vol. 31, pp. 187-191, 2002.

3.5 mm LCP™ Proximal Humerus Plate technique guide, Synthes (USA), 2002.

Titanium Wire Plate Osteosynthesis System According to Dr. Gahr internet printout, Erothitan Titanimplantate AG, print date Feb. 6, 2003.
Bilder internet printout, Martin GmbH & Co. KG, print date Sep. 5, 2003.
International Search Report for PCT Patent Application Serial No. PCT/US03/22904, Dec. 4, 2003.
The Use of a Locking Custom Contoured Blade Plate for Peri-Articular Nonunions, Harvey et al., *Injury, Int. J. Care Injured*, vol. 34, pp. 111-116, 2003.
Salvage of Distal Tibia Metaphyseal Nonunions With the 90° Cannulated Blade Plate, Chin et al., *Clinical Orthopaedics and Related Research*, No. 409, pp. 241-249, 2003.
Rib Securing Clamped Plate internet printout, Sanatmetal, print date Sep. 22, 2004.
Acromio-Clavicular Plates description page, author and date unknown.
ECT Internal Fracture Fixation brochure, Zimmer, Inc., undated.
ECT Internal Frcture Fixation System order information brochure, Zimmer, Inc., undated.
NexGen Osteotomy System (OS) surgical technique brochure, Zimmer, Inc., undated.
Spider™ and Mini-Spider™ Limited Wrist Fusion System brochure, Kinetics Medical Incorporated, undated.
Spider™ Limited Wrist Fusion System brochure, Kinetics Medical Incorporated, undated.
Zuelzer Hook Plates description page, Codman & Shurtleff, Inc., p. 808, undated.
*Biological Plating: A New Concept to Foster Bone Healing*, Synthes (USA), 1991.
Treatment by Plates of Anteriorly Displaced Distal Radial Fractures, Ducloyer, *Fractures of the Distal Radius*, pp. 148-152, 1995.
Management of Comminuted Distal Radial Fractures, Jupiter et al., *Fractures of the Distal Radius*, pp. 167-183, 1995.
Open Reduction of Intra-Articular Fractures of the Distal Radius, Amadio, *Fractures of the Distal Radius*, pp. 193-202, 1995.
May Anatomical bone Plates: Plates, Bone Screws and Instruments brochure, pp. 3-4 and 10-15, Waldemar Link GmbH & Co., 1995.
Forte Distal Radial Plate System brochure, Zimmer, Inc., 1995.
Design and Biomechanics of a Plate for the Distal Radius, Gesensway et al., *Journal of Hand Surgery*, vol. 20, No. 6, pp. 1021-1027, 1995 (abstract only provided).
*Fractures of the Distal Radius: A Practical Approach to Management*, Fernandez et al., pp. 103-188, 1996.
Titanium Distal Radius Instrument and Implant Set standard contents description pages, Synthes, Mar. 1997.
Prospective Multicenter Trial of a Plate for Dorsal Fixation of Distal Radius Fractures, Ring et al., *The Journal of Hand Surgery*, vol. 22A, No. 5, pp. 777-784, Sep. 1997.
Treatment of Displaced Intra-Articular Fractures of the Distal End of the Radius With Plates, Fitoussi et al., *The Journal of Bone and Joint Surgery*, vol. 79, No. 9, pp. 1303-1312, 1997 (abstract only provided).
The Titanium Distal Radius Plate, technique guide, Synthes (USA), 1997.
TriMed Wrist Fixation System brochure, TriMed, Inc., 1997.
SCS/D Distal Radius Plate System brochure, Avanta Orthopaedics, 1997.
Intra-Articular Fractures of the Distal Aspect of the Radius, Trumble et al., *Journal of Bone and Joint Surgery*, vol. 80A, No. 4, pp. 582-600, Apr. 1998.
Complications of the AO/ASIF Titanium Distal Radius Plate System (π Plate) in Internal Fixation of the Distal Radius: A Brief Report, Kambouroglou et al., *Journal of Hand Surgery*, vol. 23A, No. 4, pp. 737-741, Jul. 1998.
SCS/V Distal Radius Plate Volar brochure, Avanta Orthopaedics, 1998.
Delayed Rupture of the Flexor Pollicis Longus Tendon After Inappropriate Placement of the π Plate on the Volar Surface of the Distal Radius, Nunley et al., *Journal of Hand Surgery*, vol. 24, No. 6, pp. 1279-1280, Nov. 1999.
TiMAX Pe.R.I. Small Fragment Upper Extermity description pages, DePuy ACE Medical Company, 1999.

The Distal Radius Plate Instrument and Implant Set technique guide, Synthes (USA), 1999.
Outcome Following Nonoperative Treatment of Displaced Distal Radius Fractures in Low-Demand Patients Older Than 60 Years, Young, *Journal of Hand Surgery*, vol. 25A, No. 1, pp. 19-28, Jan. 2000.
Comparison of Three Different Plating Techniques for the Dorsum of the Distal Radius: A Biomechanical Study, Peine et al., *Journal of Hand Surgery*, vol. 25A, No. 1, pp. 29-33, Jan. 2000.
Distal Radial Metaphyseal Forces in an Extrinsic Grip Model: Implications for Postfracture Rehabilitation, Putnam et al., *Journal of Hand Surgery*, vol. 25A, No. 3, pp. 469-475, May 2000.
TriMed Wrist Fixation System internet description pages, TriMed, Inc., 2001.
Titanium Distal Radius Plates description page, Synthes (USA), 2001.
Locon-T Distal Radius Plating System case study and surgical method, Wright Medical Technology, Inc., 2001.
Open Reduction and Internal Fixation of Unstable Distal Radius Fractures: Results Using the Trimed Fixation System, Konrath et al., *Journal of Orthopaedic Trauma*, vol. 16, No. 8, pp. 578-585, 2002.
Locon-T Distal Radius Plating System brochure, Wright Medical Technology, Inc., 2002.
Distal Radius Fracture, Tornetta, *Journal of Orthopaedic Trauma*, vol. 16, No. 8, pp. 608-611, 2002.
Comparison of Different Distal Radius Dorsal and Volar Fracture Fixation Plates: A Biomechanical Study, Osada et al., *Journal of Hand Surgery*, vol. 28A, No. 1, pp. 94-104, Jan. 2003.
*Tendon Function and Morphology Related to Material and Design of Plates For Distal Radius Fracture Fixation: Canine Forelimb Model*, Turner et al., Orthopaedic Research Society, Feb. 2003.
Fractures of the Distal Aspect of the Radius: Changes in Treatment Over the Past Two Decades, Simic, *Journal of Bone and Joint Surgery*, vol. 85-A, No. 3, pp. 552-564, Mar. 2003.
Palmar Plate Fixation of AO Type C2 Fracture of Distal Radius Using a Locking Compression Plate—A Biomechanical Study in a Cadaveric Model, Leung et al., *Journal of Hand Surgery*, vol. 28B, No. 3, pp. 263-266, Jun. 2003.
Functional Outcome and Complications Following Two Types of Dorsal Plating for Unstable Fractures of the Distal Part of the Radius, Rozental et al., *Journal of Bone and Joint Surgery*, vol. 85, No. 10, pp. 1956-1960, 2003 (abstract only provided).
*Fixation of Unstable Fractures of the Volar Rim of the Distal Radius with a Volar Buttress Pin®*, Hooker et al., 2003.
Results of Palmar Plating of the Lunate Facet Combined with External Fixation for the Treatment of High-Energy Compression Fractures of the Distal Radius, Ruch et al., *J. Orthop. Trauma*, Vo. 18, No. 1, pp. 28-33, Jan. 2004.
Synthes Volar Distal Radius Locking Plate internet description page, Orthocopia, LLC, 2004.
VAL Plate description page, US Implants, undated.
Esser Complete Distal Fractures Radius Plate System, undated.
Proximal Humerus Fractures operative technique, Esser, undated.
MIfx Dorsal IM Plate, brochure, DVO Extremity Solutions, Sep. 2005.
Biomechanical Evaluation of the Schuhli Nut, Kolodziej, et al., *Clinical Orthopaedics and Related Research*, vol. 347, pp. 79-85, Feb. 1998.
Internal Fixation in Osteoporotic Bone, An, Y.H., p. 83, 2002.
Zespol Bone Screws, in *Mikromed—Catalogue 2004* (Nov. 2004), available at http://www.mikromed.pl/katalog/Main/main_eng.htm and http://www.mikromed.pl/katalog/zespol_eng/wkrety.htm.
Zespol Bone Plates, in *Mikromed—Catalogue 2004* (Nov. 2004), available at http://www.mikromed.pl/katalog/Main/main_eng.htm and http://www.mikromed.pl/katalog/zespol_eng/plytki.htm.
SmartLock Locking Screw Technology, advertisement, *The Journal of Hand Surgery*, vol. 30A, No. 1, Jan. 2005.
Stryker Matrix—SmartLock Procedural Guide, Stryker, Jun. 2006.
Patents Act 1977: Search Report under Section 17 from United Kingdom Patent Application No. GB 07 12931.5, applicant Acumed LLC, dated Aug. 1, 2007, Examiner Alex Robinson, pp. 1-2.

\* cited by examiner

BONE PLATES WITH INTRAOPERATIVELY TAPPED APERTURES

CROSS-REFERENCE TO PRIORITY APPLICATION

This application is based upon and claims the benefit under 35 U.S.C. § 119(e) of U.S. Provisional Patent Application Ser. No. 60/480,529, filed Jun. 20, 2003, which is incorporated herein by reference in its entirety for all purposes.

INTRODUCTION

The human skeleton is composed of 206 individual bones that perform a variety of important functions, including support, movement, protection, storage of minerals, and formation of blood cells. These bones can be grouped into two categories: the axial skeleton, and the appendicular skeleton. The axial skeleton consists of 80 bones that make up the body's center of gravity, and the appendicular skeleton consists of 126 bones that make-up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton, among others.

Bones of the skeleton may become fractured in response to trauma. To ensure that the skeleton retains its ability to perform its important functions, and to reduce pain and disfigurement, fractured bones should be repaired promptly and properly. Typically, fractured bones are treated using fixation devices, which reinforce the fractured bones and keep them aligned during healing. Fixation devices may take a variety of forms, including casts for external fixation and bone plates for internal fixation, among others. Casts are minimally invasive, allowing reduction and fixation of simple fractures from outside the body. In contrast, bone plates are sturdy internal devices, usually made of metal, that mount directly to the bone adjacent the fracture.

Bone plates may be used to repair a fracture, as follows. First, a surgeon selects an appropriate plate. Second, the surgeon reduces (sets) the fracture. Finally, the surgeon fastens the plate to opposite sides of the fracture using suitable fasteners, such as screws and/or wires, so that the bone is fixed in position. The mounted plate may be left in place permanently, or it may be removed after the bone has healed sufficiently.

Bone plates typically include a plurality of apertures for receiving fasteners such as bone screws. These apertures may be nonthreaded or threaded.

Nonthreaded apertures may be used to provide compression at a selectable angle of fastener placement. Specifically, a bone screw inserted through a nonthreaded aperture will thread into the bone but not the bone plate. Thus, the screw will turn without limitation until the bone plate and bone are brought into contact, or compressed. Furthermore, variable angle screws may be used in conjunction with nonthreaded apertures. This may allow the angle with which the screw enters the bone to be chosen by the surgeon intraoperatively.

Threaded apertures, in contrast, may be used to lock the screw into the plate and buttress the bone. Specifically, a bone screw inserted through a threaded aperture will thread into both the plate and bone. Thus, there may be a space between the plate and bone if the screw is threaded fully into the plate (such that the screw cannot turn any more) before compression occurs between the bone and the plate. The space may have several advantages, such as facilitating healing by preserving blood flow to the bone, and, in the case of a removable bone plate, reducing undesirable bonding of the plate to the bone. However, a threaded aperture typically limits the angle of installation of the screw, since the threads provide a fixed orientation for engagement between the screw and the aperture. A fixed screw also may act as a buttress in the bone to reduce malunion due to bone resorption.

Bone plates are provided with nonthreaded or threaded apertures based on the best guesses of manufacturers regarding the most suitable apertures for a given indication. Thus, surgeons currently may be limited to using plates designed only for the most common fractures. However, although many fractures share common motifs, no two fractures or bones are identical. In some cases, a surgeon may want a threaded aperture where a nonthreaded aperture is provided, or vice versa. Similarly, a surgeon may find it desirable to insert a screw through a threaded aperture, but at a specific angle that is not provided by a conventional bone plate.

SUMMARY

The present teachings provide systems, including apparatus, methods, and kits, for selectively tapping apertures of bone plates, to form threaded apertures during installation of the bone plates (i.e., intraoperatively).

DETAILED DESCRIPTION

The present teachings provides systems, including apparatus, methods, and kits, for selectively tapping apertures of bone plates, to form threaded apertures during installation of the bone plates (i.e., intraoperatively). These systems may allow a surgeon to choose independently between threaded and nonthreaded engagement with a fastener for different apertures of the bone plates, so that each fastener can be locked or not locked, respectively, to the plates. Moreover, these systems may allow the surgeon to choose the angle at which fasteners engage the bone plate and bone, by allowing the apertures to be tapped at selected angles.

Figure 1:
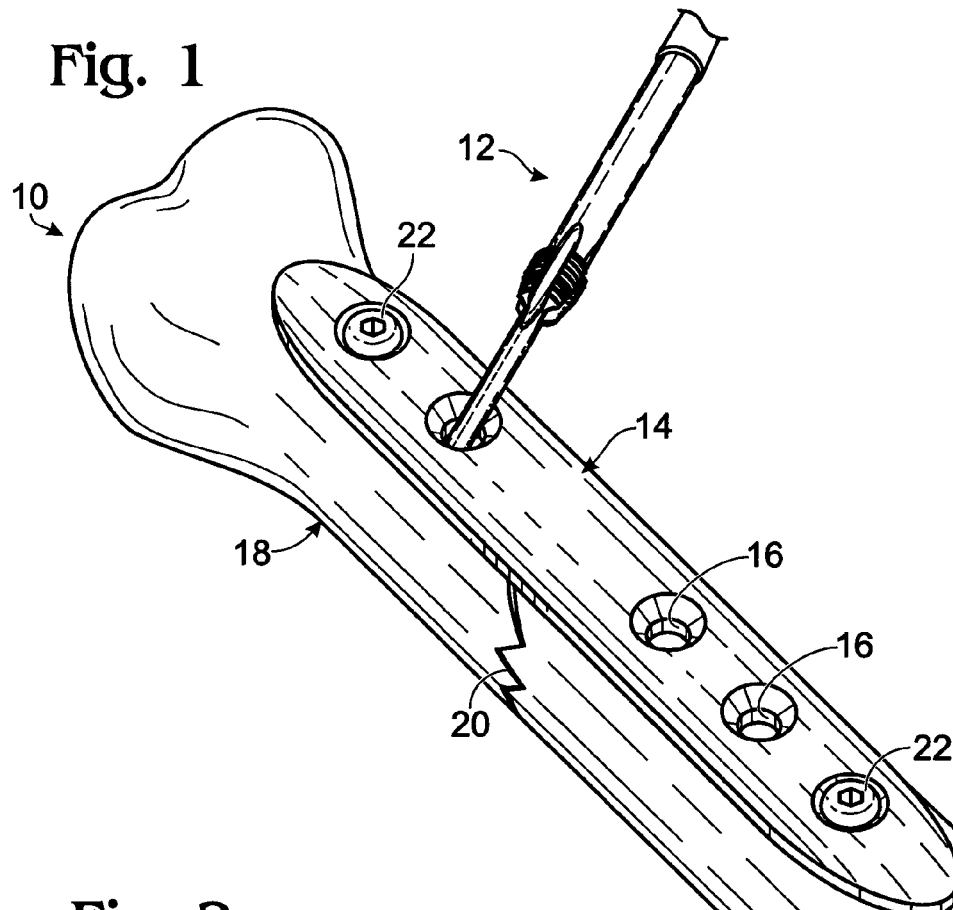
FIG. 1 is a perspective view of a system for tapping bone plates intraoperatively, including an exemplary tap device being positioned for tapping an aperture of a bone plate while the bone plate is disposed on a surface of a bone, in accordance with aspects of the present teachings.
Figure 2:
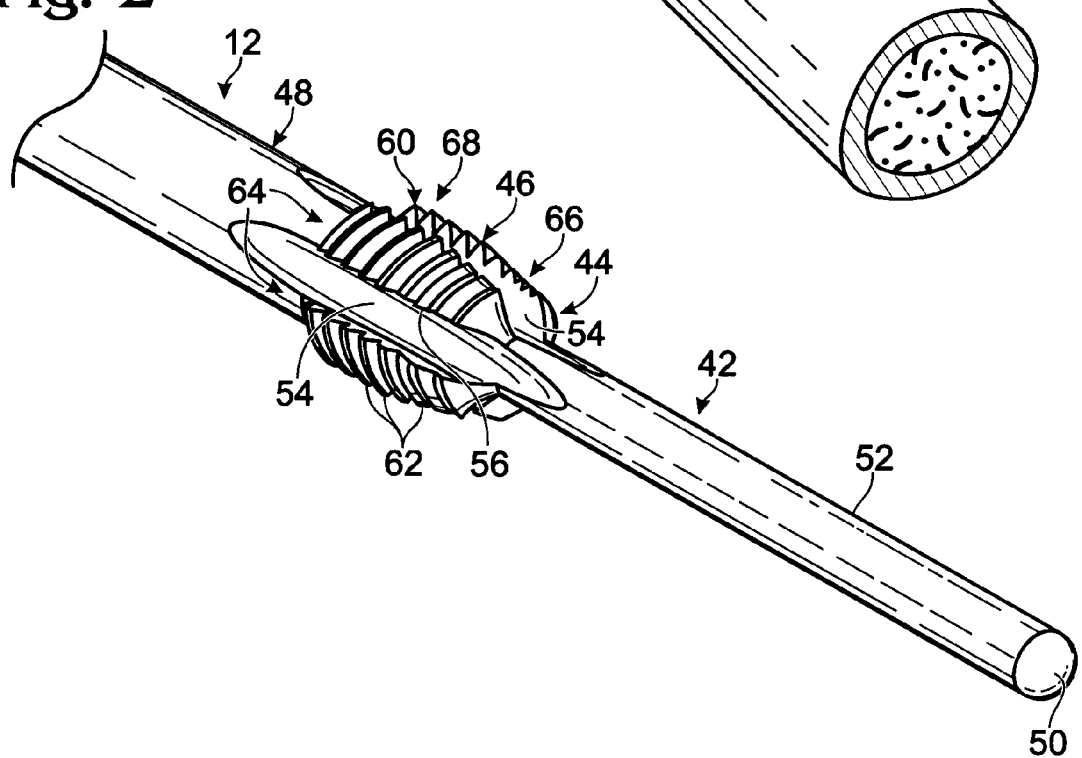
FIG. 2 is a fragmentary perspective view of a distal portion of the tap device of FIG. 1.

FIG. 1 shows an exemplary system 10 for intraoperatively tapping an aperture(s) of a bone plate. The system may include, among others, (1) a tap device 12, (2) a bone plate 14 having one or more apertures 16, and (3) fasteners to be received in tapped and/or nontapped apertures of the bone plate. The tap device may be used to form a thread in (to tap) any suitable number of the apertures of the bone plate. Each aperture may be threaded or nonthreaded before intraoperative tapping is performed. Furthermore, one or more (or all) apertures may be sized/shaped to be tapped intraoperatively with the tap device, and one or more (or no) apertures may be sized/shaped so that they cannot be tapped readily with the tap device. In some embodiments, an aperture(s) may be formed and tapped in a bone plate by the tap device. In some examples, the tap device may drill, ream, and/or tap bone underlying each aperture. Further aspects of tap devices and their uses in general, and tap device 12 and its uses in particular, are included below in Sections I and III, among others.

The bone plate may be disposed on a bone 18, adjacent a suitable surface of a bone. The suitable surface may be disposed on diaphyseal bone (the shaft of the bone) and/or on metaphyseal bone (near an end of the bone). In some embodiments, intraoperative tapping adjacent metaphyseal bone may be more suitable, due, for example, to the greater complexity in shape and/or breakage patterns in metaphyseal regions. The bone may have at least one discontinuity, such as a fracture 20, which may be spanned by the bone plate, and/or the bone plate may strengthen a bone lacking a discontinuity, among others. The bone plate may be connected to the bone with suitable fasteners, such as one or more bone screws 22 received in apertures of the bone plate and engaged with underlying bone. In some examples, the fasteners may be positioned to secure the bone plate to the bone on only one side or on opposing sides of the discontinuity. In some embodiments, the fasteners may include a wire, a clamp, a pin, and/or the like. In any case, the fasteners may hold the bone plate in position on the bone provisionally, as the bone plate is being tapped at one or more apertures (and then removed/replaced), or for an extended period, such as during healing of the bone, among others.

The apertures to be tapped (i.e., threaded) in a plate, and the angles at which the apertures are tapped, may be selected. Selection may be performed during surgery, based on x-ray (or other) imaging data, direct observation, trial fitting, and/or placement of a guide device, among others. The use of bone screws in conjunction with one or more threaded apertures of a bone plate may allow at least a portion of the plate to be optionally positioned as a buttress, away from the bone. This may allow periostea, blood vessels, and/or the like to pass under the plate without being pinched or damaged, possibly promoting faster healing. Positioning the plate slightly away from the bone further may allow for some amount of natural settling and/or thickening (e.g., through calcification) of the fractured bone. Accordingly, the present teachings may provide greater flexibility in placement of bone screws into bone (such as metaphyseal bone), improved attachment of bone screws to bone plates and/or to bone, and/or improved fixation and healing of injured bones, among others.

Further aspects of the present teachings are included in the following sections, including, among others, (I) tap devices, (II) fasteners for tapped apertures, (III) methods of tapping apertures and of securing bone plates to bones, (IV) bone plates, (V) guide devices, (VI) kits, and (VII) examples.

I. Tap Devices

The systems of the present teachings provide tap devices. A tap device may include any structure that can be manipulated or operated to form a thread(s) in a bone plate, particularly while the bone plate is disposed on a bone. The tap device also may be configured to form and/or follow a hole in bone and/or in the bone plate, to widen a hole in the bone (and/or in the bone plate), and/or to reduce or draw out "chips" (i.e., bone and/or plate material removed by the tap device), among others. The tap device may be solid or may be partially or completely hollow, for example, cannulated with an axial bore. The tap device may include a tip portion, a reamer portion, a tap portion, and a driven portion, among others. Any two or more of these portions may be coupled to one another in a fixed or a movable (such as a rotatable) relationship. In some examples, these portions may be formed integrally as one piece, for example, as a tapping bit. In some examples, the tap device also may be configured to secure the bone plate to bone, such as a bone screw having a tapping structure included in the head of the bone screw.

The tap device may be formed of any suitable material hard enough to cut a thread in the bone plate and/or bone. Accordingly, the material for the tap device may be selected, for example, based on the composition of the bone plate. The material also may be rigid enough to transmit a torque from the driven portion of the tap device to the tap portion, and to remain generally nondeformed during tapping operations. Exemplary materials for the tap device may include metal, ceramic, plastic, composite, and/or the like.

The tip portion, also termed a guidance tip, may be disposed at a leading end (a distal region) of the tap device, to guide the tap device into bone. The tip portion may help to stabilize the tap device and to hold it at a fixed angle relative to the bone, while tapping takes place. Alternatively, or in addition, the tip portion may facilitate penetrating the bone at a desired angle to produce a pilot hole in the bone, or may follow, widen, and/or deepen all or part of a preexisting pilot hole. The tip portion may be rigid enough not to be deformed substantially as it guides the tap portion to the bone plate.

The tip portion may have any suitable shape and size. The tip portion may be generally linear or may be nonlinear, such as helical or curved. The tip portion may be generally cylindrical, having a smooth, textured, and/or contoured surface. A distal end region of the tip portion may be rounded, tapered, and/or or pointed, among others. In some examples, the tip portion may include drilling structure, so that the tip portion also can form a hole in bone as the tip portion enters bone. In this case, the tip portion may include a cutting edge, a helical channel, and/or a distal end region that is sharp, among others. The tip portion may have any suitable length, measured axially in the tap device. Generally, the tip portion may be at least as long as the tap portion, and may be at least about twice or three times as long as the tap portion, among others. Furthermore, the tip portion may have a length selected according to the length of the shaft of a bone screw to be used with the tap device. For example, the tip portion may have a length that is about as long as, shorter than, or longer than, the length of the shaft of the bone screw to be placed in an aperture tapped by the tap device. In some embodiments, the tip portion may have a length of about 5 mm to 100 mm, with particular exemplary lengths of about 8 mm, 25 mm, and 50 mm, among others. The tip portion may have any suitable diameter, generally a diameter less than the diameter of the tap portion and less than the crest-to-crest diameter of a threaded shaft of a fastener to be placed in an aperture tapped by the tap portion. In some examples, the diameter of the tip portion may be less than about one-half the diameter of the tap portion. In some embodiments, the tip portion may have a diameter of about 1.5 mm to 4.0 mm, among others.

The reamer portion may be configured to widen a hole in bone followed and/or formed by the tip portion. Accordingly, the reamer portion may be included in the tip and/or tap portions or may be disposed between the tip portion and the tap portion (such as adjoining the tap portion), among others. The reamer portion may taper from the tap portion toward the tip portion, and thus may have a generally frustoconical shape. The reamer portion may include one or more cutting flutes extending, for example, generally axially on the tap device.

The tap portion may be used to form a thread in a bone plate aperture and/or in underlying bone. The tap portion may include an external thread or threaded region to guide cutting surfaces of the tap portion along a helical path to form an internal thread in the aperture and/or in the bone. The external thread or threaded region may have any suitable number of thread segments arrayed generally axially, such as at least one, two, three, or more. The tap portion may taper toward a distal section of the tap device (toward the tip portion), so that a thread cut by the tap portion becomes shallower toward the tip portion, particularly in bone. Accordingly, the external thread/threaded region of the tap portion may have flatter/shorter crests distally. The tap portion may include one or more cutting flutes intersecting the external thread or threaded region, for example, extending axially on the tap device. The cutting flutes of the tap portion may abut cutting flutes of the reamer portion. In some examples, the tap portion (or an adjacent, proximal region of the tap device) may include a stop structure, such as a widened region or a transverse extension, that contacts the bone plate, to restrict excessive advancement of the tap portion through the bone plate. In some examples, the stop structure may have an adjustable axial position.

The driven portion may be configured to be coupled to a driver so that the tap device can be rotated. The driver may include any suitable turning mechanism, such as a power-driven or manually operated driver, and/or a manually operable lever or hand crank, among others. The driven portion may include a shaft that extends proximally from the tap portion. The shaft may be cylindrical or noncylindrical. In some examples, the shaft may be at least as long as the tap portion, or at least twice as long, among others. The driven portion also may include, for example, a recess, a boss, a ridge, a groove, a thread, and/or a beveled/flattened section, among others, to facilitate engagement with the driver.

FIGS. 2 and 3A-C show various views of tap device 12 from FIG. 1. The tap device 12 may include a tip portion 42, a reamer portion 44, a tap portion 46, and a driven portion 48.

The tip portion 42 may be shaped to follow a pilot hole formed in bone. The tip portion 42 may include a rounded leading or distal end 50 and a cylindrical following or proximal section 52. The tip portion may be at least substantially or completely nonthreaded along its length.

The reamer portion 44 may flare outward as it extends away from the proximal section 52 of the tip portion. The reamer portion may abut the tap portion 46 and may share a plurality of axial flutes 54 with the tap portion. An edge of each flute may define a cutting edge 56 where the flute meets the reamer portion (or the tap portion). The flutes also may extend into the tip portion and/or the driven portion.

The tap portion 46 may include a thread (or threads) 60 having a plurality of adjacent thread segments 62. The thread segments may be grouped into segment sets 64 separated by flutes 54 (see FIGS. 3B and 3C). The thread may taper toward the tip portion. For example, distal thread segments, shown at 66, may be shorter and/or blunter than proximal thread segments, shown at 68 (see FIG. 3B).

Figure 3A:
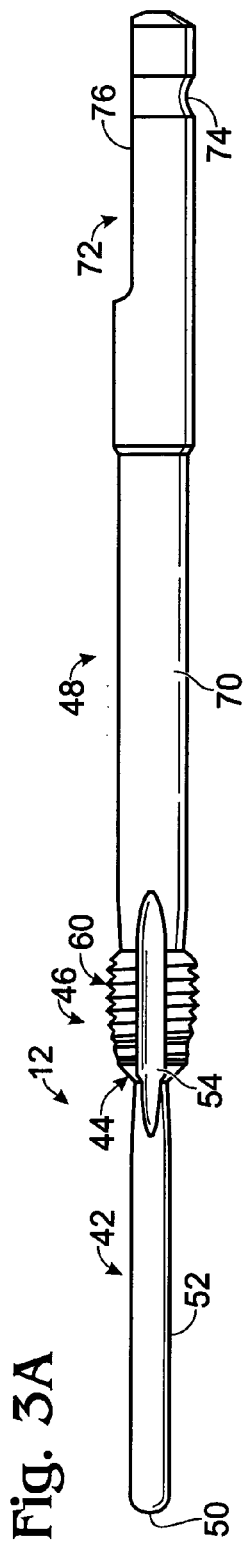
FIG. 3A is a side elevation view of the tap device of FIG. 1.
Figure 3C:
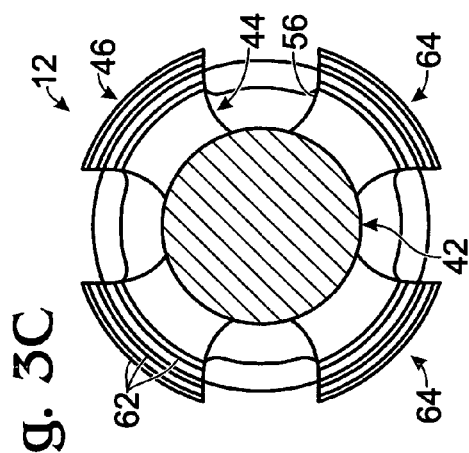
FIG. 3C is a sectional view of the tap device of FIG. 1, taken generally along line 3C-3C of FIG. 3B.
Figure 3B:
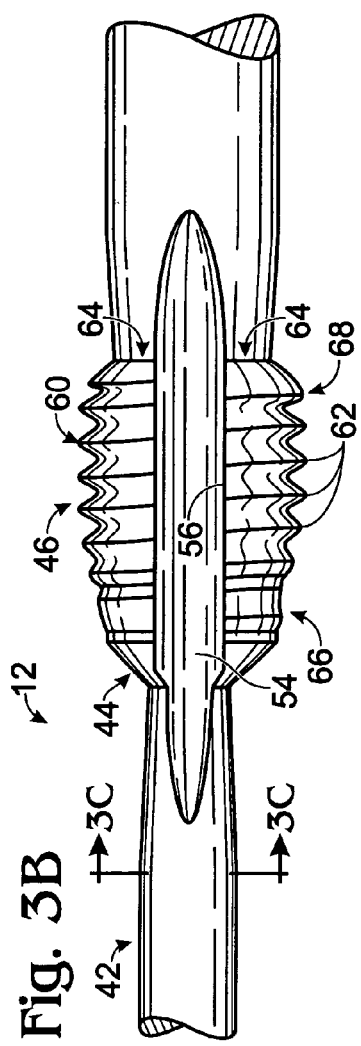
FIG. 3B is a fragmentary side elevation view of selection portions of the tap device of FIG. 1, particularly a tap portion of the tap device.

The driven portion 48 may include a spacer or shaft 70 and an interface region 72 engaged by a driver (see FIG. 3A). The interface region 72 may include an annular groove 74 and/or a planar recess 76, among others.

Figure 4:
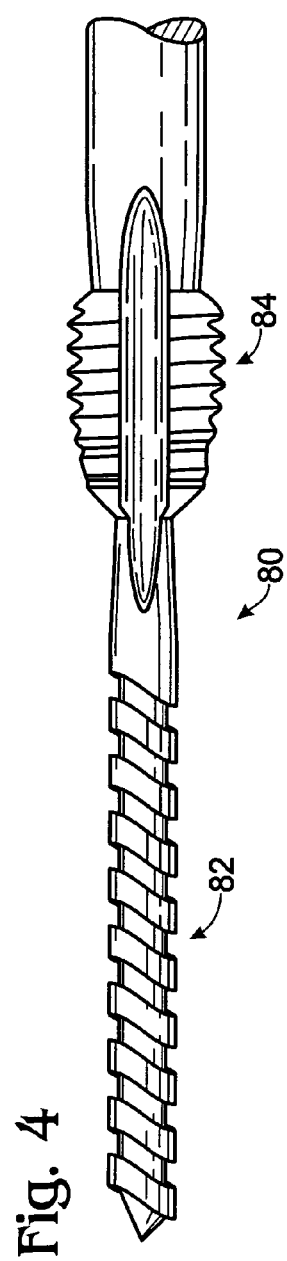
FIG. 4 is a fragmentary side elevation view of another exemplary tap device for intraoperatively tapping an aperture of a bone plate, in accordance with aspects of the present teachings.

FIG. 4 shows another exemplary tap device 80 for intraoperatively tapping an aperture of a bone plate. Tap device 80 may include a tip portion 82 configured as a drill bit, to form a hole in the bone (and/or bone plate) before and/during tapping performed by a tap portion 84 of the tap device.

II. Fasteners for Tapped Apertures

The systems of the present teachings may provide fasteners to be received in tapped apertures, particularly apertures tapped by a tap device as described in Sections I and III. The fasteners, such as bone screws, may include a head and a shank, each of which may be threaded or nonthreaded. The fasteners may be solid or partially or completely hollow (i.e., cannulated with an axial bore)

The head may have any suitable size and structure. For example, the head may have any suitable diameter, generally at least as great as, or greater than the diameter of the shank. The diameter may correspond to the diameter of a tapped aperture, so that at least a portion of the head fits closely into the tapped aperture. In some embodiments, the diameter of the head may be about 3 mm to 7 mm. The head may have any suitable length, measured axially on the fastener. For example, the length of the head may be less than, about the same as, or greater than the thickness of a bone plate for which the fastener is configured. In some embodiments, the head may have length sufficient for a proximal (or intermediate) region of the head to be disposed in a tapped aperture of the bone plate and for a distal region of the head to be disposed in bone. In some examples, a proximal portion of the head may protrude above the bone plate when the fastener is fully installed. In some embodiments, the length of the head may be about 2 mm to 6 mm, among others. The head may include tool engagement structure, such as a hexagonal socket, a linear slot, a cruciform slot (with or without a deeper central depression), or the like, so that a tool can engage the head and transmit torque to the head and shank. The head may include a thread(s) extending along any suitable portion of its length. The thread may be an external (male) thread configured to be threadably engaged with the internal (female) thread of a tapped aperture and/or underlying bone. The thread may include any suitable number of thread segments arrayed axially, generally at least two or more. In some examples, the head may include at least three or at least four of such thread segments. The thread segments may form a continuous thread and/or a discontinuous thread (for example, interrupted by axial flutes).

The head also may include a shoulder region, a cap region, and/or tapping structure. The shoulder region may join the head to the shank. The shoulder region may taper toward the shank, for example, so that the shoulder region is generally frustoconical, or may be nontapered. The shoulder region may be threaded or nonthreaded. A cap region may be disposed proximally on the head. The cap region may be configured to restrict excessive advancement of the head through a tapped aperture. Accordingly, the cap region may be nonthreaded and/or may have an increased diameter relative to an adjacent threaded region of the head. A tapping structure of the head may be configured to form and/or deepen a thread in the bone plate and/or adjacent bone. The tapping structure may be disposed, for example, at a leading (distal) section of the head. Exemplary tapping structure may include one or more flutes extending generally axially relative to the head and intersecting a threaded region thereof.

The shank may have any suitable size and structure. The shank may have any suitable length. For example, the shank may be shorter than, at least as long as, or longer than the head. In some examples, the shank may be at least twice as long as the head. In some embodiments, the shank may be about 5 mm to 100 mm in length, with particular exemplary lengths including 8 mm, 10 mm, 25 mm, 50 mm, or 70 mm, among others. The shank may be long enough to extend through bone to an opposing bone cortex (for a bicortical fastener), to extend into cancellous bone, and/or to terminate in the cortex adjacent the bone plate (for a unicortical fastener). In some embodiments, the shank may be absent from the fastener. The shank may include a thread(s) disposed along any suitable portion of the shank's length, such as at least substantially the entire length of the shank. The thread may have the same pitch as a thread on the head or may have a different pitch, that is, a smaller or larger pitch that is constant or variable. The shank may include tapping structure configured to form and/or deepen a thread in the bone, such as in a pilot hole used to guide a tap device. The tapping structure may be disposed, for example, at a leading (distal) section of the shank. Exemplary tapping structure may include one or more cutting flutes extending generally axially relative to the shank and intersecting a threaded region thereof.

Exemplary fastener sizes and pitches that may be suitable are included in the following patent application, which is incorporated herein by reference: U.S. Provisional Patent Application Ser. No. 60/548,685, filed Feb. 26, 2004.

Figure 5:
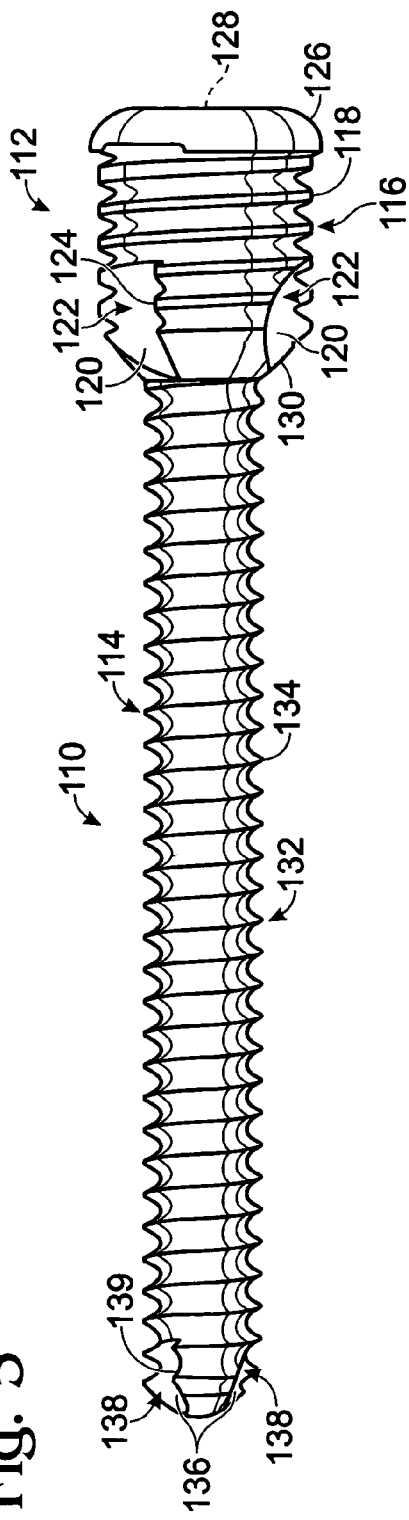
FIG. 5 is a side elevation view of an exemplary bone screw that may be threadably engaged with a thread of an aperture intraoperatively tapped by the system of FIG. 1, in accordance with aspects of the present teachings.

FIG. 5 shows an exemplary bone screw 110 that may be threadably engaged with an intraoperatively tapped aperture, for example, an aperture tapped with the tap devices of FIGS. 1-4. Bone screw 110 may include a head 112 and a shank 114.

The head 112 may include any suitable structures. For example, the head may include a threaded region 116 extending over a majority of the length of the head. The threaded region 116 may include a thread 118, which may be intersected by a plurality of flutes 120 to form tapping structures 122 each having a cutting edge 124. The head also may include a cap region 126 forming a proximal region of the head. Furthermore, the head may include a tool engagement structure 128 for imparting torque to the bone screw, and a shoulder 130 forming a transition between the head and the shank.

The shank 114 may include any suitable structures. For example, the shank may include a threaded region 132 having a thread 134. Furthermore, a distal end of the shank may include one or more flutes 136 to form one or more tapping structures 138 each having a cutting edge 139.

Figure 6:
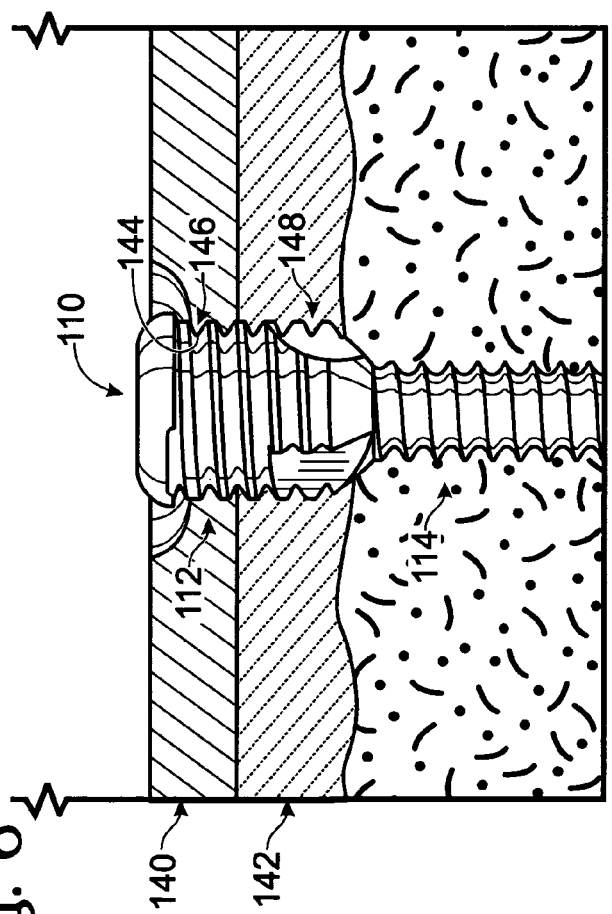
FIG. 6 is a partially sectional view of the bone screw of FIG. 5 placed into threaded engagement with a bone plate and bone, in accordance with aspects of the present teachings.

FIG. 6 shows bone screw 110 disposed in threaded engagement with a bone plate 140 and bone 142. A proximal region of the head 112 may be threaded into a tapped aperture 144 of the bone plate, shown at 146. The head may be flush with the outer surface of the bone plate, disposed below this outer surface, or may project somewhat above the outer surface of the bone plate, as shown in the present illustration. A distal region of the head may be threaded into a tapped cortical region of the bone, shown at 148. The shank 114 may extend into an underlying/opposing cortical, cancellous, and/or medullary region of bone 142, for example, to be disposed in threaded engagement with the bone.

III. Methods of Tapping Apertures and of Securing Bone Plates to Bones

The systems of the present teachings also provide methods of tapping apertures and/or of securing bone plates to bones. These methods may include, among other steps, any suitable combination of the following steps, performed in any suitable order, any suitable number of times: (1) selecting a bone plate, (2) positioning the bone plate on a bone, (3) connecting the bone plate to the bone, (3) forming a pilot hole in the bone, (4) tapping an aperture(s) of the bone plate, and/or (5) placing a fastener(s) into the aperture(s). These methods may permit a surgeon to determine, aperture by aperture, the spacing between the plate and bone, locked and nonlocked engagement of each fastener with the bone plate, and/or the angle(s) with which fasteners extend through the bone plate and into bone. Thus, the methods described herein may provide surgeons with more options for installation of bone plates, which may lead to more secure and/or appropriate fixation of the plates.

FIGS. 7-12 show exemplary configurations of a bone plate, a bone, and bone screws that may be created by performing exemplary steps of methods of tapping apertures and/or of securing bone plates to bones. These configurations are described in the following paragraphs relative to the method steps listed above.

A bone plate may be selected. The bone plate may be preshaped for a particular target bone or bone region, and/or may be shaped/adjusted intraoperatively. The bone plate may have any suitable number of apertures, including none, one, or more, and the apertures may be similar in shape and/or size, or may be of two or more different shapes and/or sizes to facilitate tapping intraoperatively and/or to direct placement of bone screws without intraoperative tapping. Apertures configured to be tapped may include a wall region (a land) extending generally orthogonal to a local length-by-width plane defined by the bone plate, such as a wall region forming a cylindrical bore. A counterbore may be disposed adjacent the wall region so that the aperture flares outward toward the outer surface of the bone plate.

Figure 7:
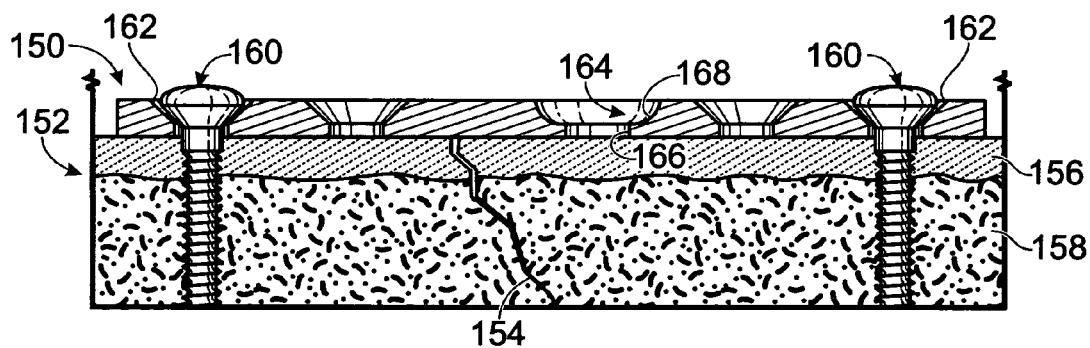
FIGS. 7-12 are partially sectional views of exemplary configurations of a bone plate, a bone, and bone screws created by performing steps of a method of securing a bone plate to a bone, in accordance with aspects of the present teachings.

The bone plate may be positioned on a bone. The bone plate may be disposed on a surface of the bone and may span a discontinuity in the bone, by extending axially and/or transverse to the bone. For example, FIG. 7 shows an axial sectional view of a bone plate 150 disposed on a surface of a bone 152 having a fracture 154. The plate may be disposed over a region of bone having a cortex 156 and a medullary canal 158 and/or may be spaced from the medullary canal of the bone (such as adjacent a metaphyseal region near an end of a bone).

The bone plate may be connected to the bone. This step of connecting may be performed to limit movement of the bone plate relative to bone during intraoperative tapping and/or subsequent fastener placement. Accordingly, the step of connecting may secure the bone plate to the bone so that the bone plate is fixed in position. The step of connecting may be performed with one or more fasteners, such as screws, pin, wires, etc., placed through apertures of the bone plate. For example, FIG. 7 shows bone plate 150 secured to bone 152 using bone screws 160 received in apertures 162 that flank an aperture 164 to be tapped. Any suitable aperture(s) may be selected for the step of connecting. The apertures selected may be tappable intraoperatively (or may have already been tapped intraoperatively), or may be sized/shaped so that they are not suitable to be tapped intraoperatively. Alternatively, or in addition, the bone plate may be secured with a clamp device, such as that described in Section V.

The bone plate may have at least one tappable aperture 164. The tappable aperture may include a generally orthogonal wall or a land 166 into which a thread(s) may be formed during intraoperative tapping. The land may define a lip of the aperture. In the present illustration, wall 166 defines a cylindrical region of the aperture. Aperture 164 also or alternatively may include a counterbore 168, such as the radiused or generally frustospherical counterbore shown here. Such a counterbore may be formed, for example, with a balling mill. In the present illustration, tappable aperture 164 has a distinct configuration relative to other apertures 162 of the bone plate. Accordingly, tappable apertures may be visibly distinct and/or may be marked with indicia to indicate that they are configured to be tapped. Alternatively, in some embodiments, all the apertures of a bone plate may be similar in structure and configured to be tapped.

A pilot hole may be formed in the bone. The pilot hole may be formed with a hole-forming tool such as a drill and/or by a tap device having a hole-forming structure. The pilot hole may be formed in alignment with an aperture of the bone plate, for example, generally centered below the aperture. The pilot hole may be formed orthogonal to the bone plate or at a selected angle relative to the bone plate. The angle of the pilot hole may determine a corresponding angle at which a bone screw will subsequently engage a newly tapped aperture. This angle thus may be selected by a surgeon during surgery, rather than being predetermined as in the case of a pre-threaded aperture. The pilot hole may have a diameter greater than the diameter of a tip portion of the tap device and less than the diameter of a shank of a bone screw to be placed in to the pilot hole. The pilot hole may have any suitable depth and may extend unicortically, bicortically, and/or into cancellous bone, among others.

Figure 8:
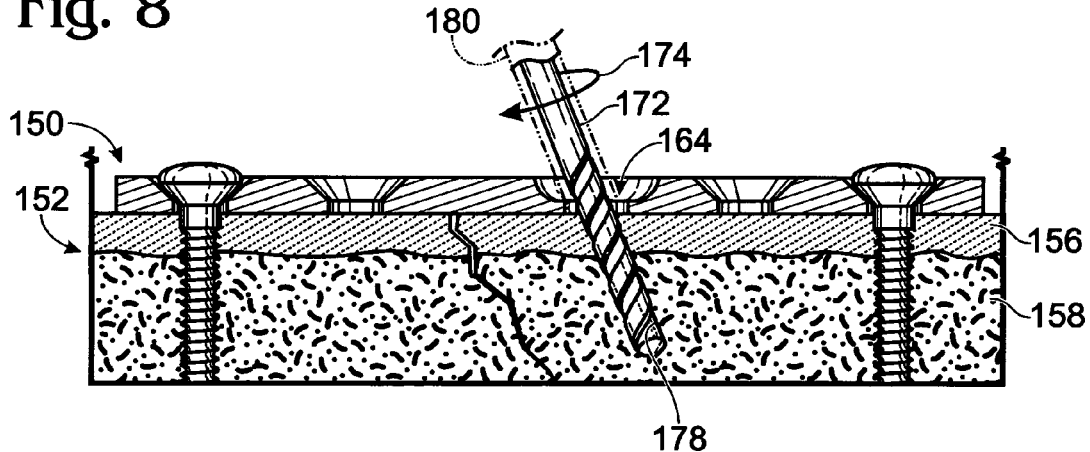

FIG. 8 shows an exemplary configuration produced during a step of forming a pilot hole in the bone. A drill 172 may be driven rotationally, shown at 174, and advanced axially through tappable aperture 164 to form a pilot hole 178. The drill 172 may be disposed at a selected oblique angle (or orthogonally) relative to the bone surface. The drill 172 may be advanced through the cortex 156 and into the medullary canal 158 (and/or into cancellous bone and/or into/through an opposing cortex). The depth of hole formation may be determined, for example, by a stop disposed on the drill, by depth indicia on the drill or on a measuring device, by visual observation, and/or the like. In some examples, the drill may be guided by a guide device, such as a hand-held cannula 180 disposed in engagement with the bone plate around the tappable aperture 164.

Figure 9:
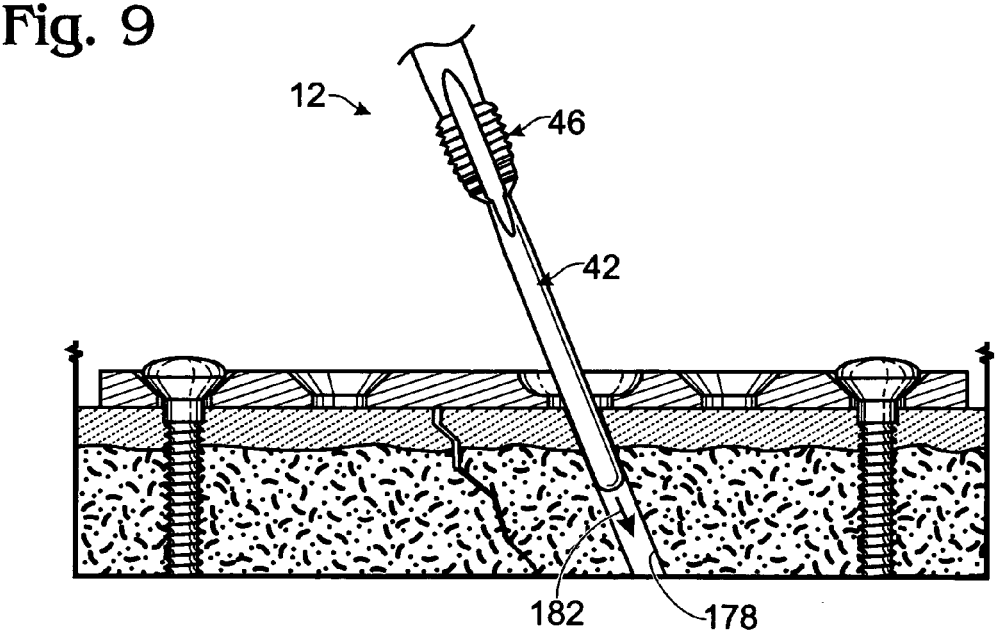
Figure 10:
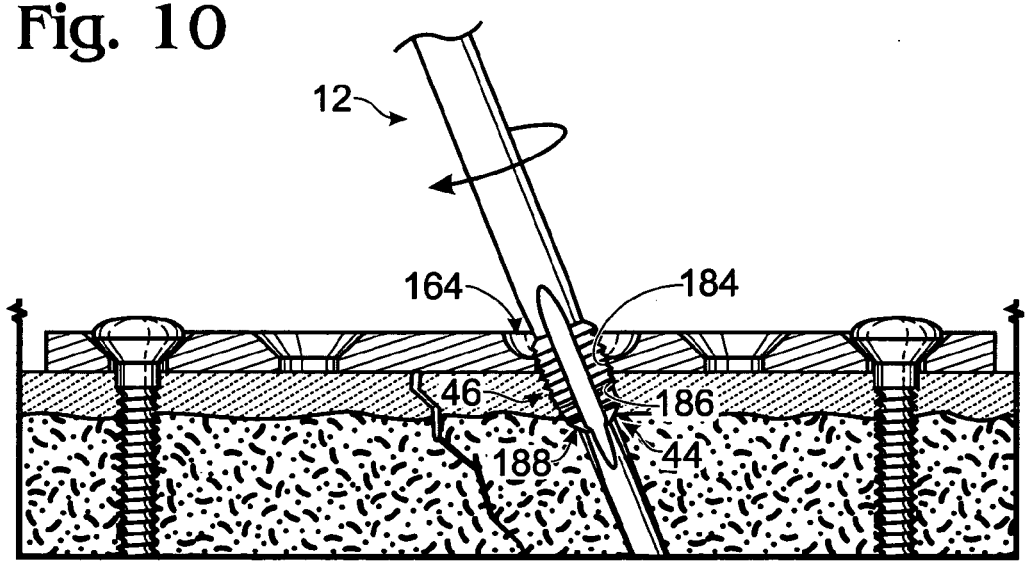

An aperture of the bone plate may be tapped to form a thread in the aperture. The aperture may be tapped using a tap device. The aperture may be tapped with the plate positioned away from the bone (such as with the plate disposed on a rack or frame), and/or it may be tapped in situ, with the plate positioned adjacent the bone. A tip portion of the tap device may be received in a pilot hole to guide a tap portion of the tap device to an aperture. The tip portion may follow a pre-formed pilot hole, may form the pilot hole, and/or may widen the pilot hole. For example, FIG. 9 shows tip portion 42 of tap device 12 being advanced axially along pilot hole 178, shown at 182. The tap device may be rotated so that the tap portion 46 taps a wall of the aperture and, optionally, underlying bone, particularly cortical bone. The tap device may tap the aperture at least substantially symmetrically, for example, evenly tapping the walls of a circular aperture, allowing for up to full threaded engagement of a fastener with the aperture. Alternatively, the tap device may tap the aperture asymmetrically, for example, tapping an end, and optionally the adjacent sides, of an elongated aperture, leaving the other end, and optionally the adjacent sides, untapped, allowing for partial threaded engagement of a fastener with the aperture. For example, FIG. 10 shows tap device 12 with tap portion 46 in engagement with the bone plate and underlying cortical bone, to form a thread 184 in aperture 164 and extending into the bone, shown at 186. Because the tap portion may be tapered, the thread formed in bone may be shallower than in the bone plate. The reamer portion 44 of the tap device may widen the pilot hole and/or the aperture of the bone, shown at 188. Tapping may be terminated based a visible position of the tap device and/or a marking(s) thereon, using a stop mechanism, based on image (such as X-ray) analysis, trial placement of a fastener, and/or the like.

Figure 11:
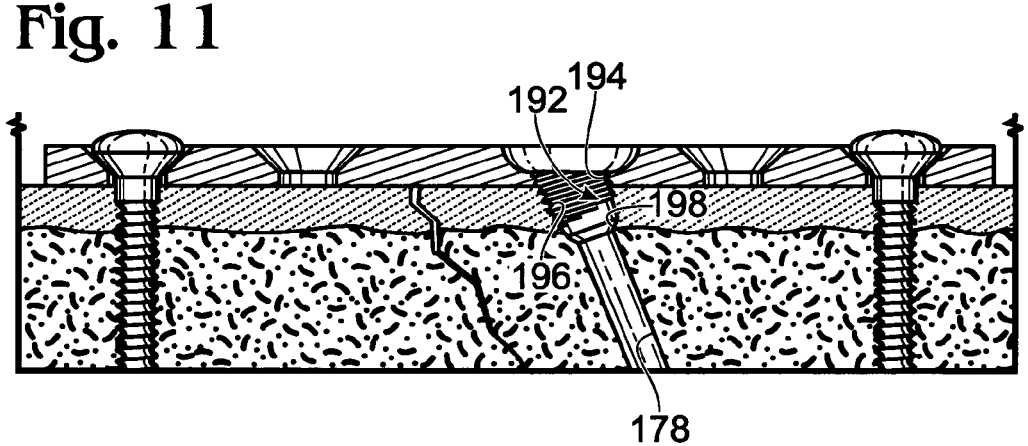

The tap device may be removed after the aperture has been tapped. For example, FIG. 11 shows a tapped bore 192 formed by the tap device. The tapped bore may include a tapped aperture 194 of the bone plate and tapped bone 196 formed adjacent the tapped aperture. The tapped bore also may narrow distally, shown at 198, as it joins the pilot hole 178. Alternatively, the tap device may be left in position after the aperture has been taped, for example, when a bone screws taps the aperture of the bone plate.

Figure 12:
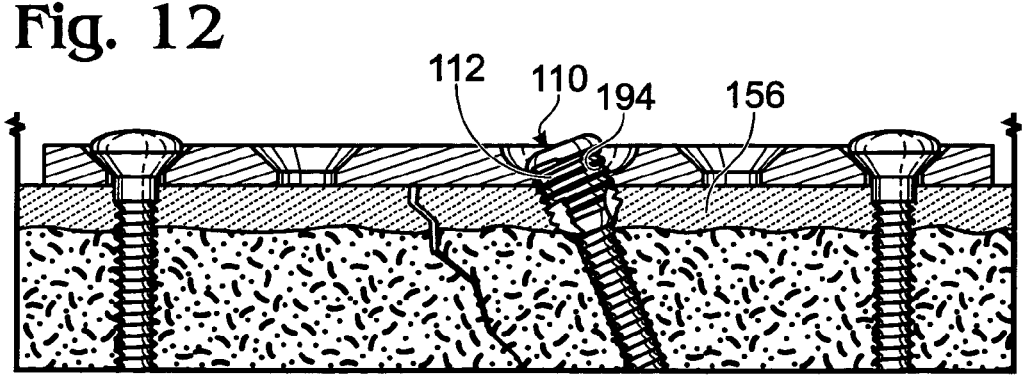

A fastener may be placed into the tapped aperture and into the bone. The fastener may be advanced rotationally into the tapped bore and pilot hole, to lock the fastener to the bone plate and to engage bone. For example, FIG. 12 shows bone screw 110 in threaded engagement with tapped aperture 194 and cortical bone 156, through the head 112 of the bone screw. Accordingly, the head may be placed into threaded engagement with a pre-existing thread in both the bone plate and the bone. The shank of the bone screw may be in threaded engagement with adjacent/opposing bone, such as the same cortex and/or the opposing cortex of the bone.

Fasteners then may be placed into other apertures of the bone plate. These fasteners may be placed into intraoperatively tapped apertures and/or into nontapped apertures.

IV. Bone Plates

Bone plates for intraoperative tapping generally comprise any relatively low-profile (or plate-like) fixation device configured to stabilize at least one bone by attachment to the bone. The fixation device may be configured to span any suitable bone discontinuity (or discontinuities) so that the fixation device fixes the relative positions of bone pieces/fragments (and/or bones) disposed on opposing sides of the bone discontinuity (or discontinuities). Alternatively, or in addition, the fixation device may reinforce a bone lacking a discontinuity.

Suitable discontinuities may occur naturally and/or may result from injury, disease, and/or surgical intervention, among others. Accordingly, exemplary discontinuities for use with the fixation devices described herein may include joints, fractures (breaks in bones), osteotomies (cuts in bones), and/or nonunions (for example, produced by injury, disease, or a birth defect), among others.

The bone plates to be tapped intraoperatively may be configured for use on any suitable bone, in any suitable species, including human, equine, canine, and/or feline species, among others. Exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, ribs, and/or clavicles, among others.

Each bone plate may be configured to be disposed in any suitable position relative to its target bone. The bone plate (or a plate portion) may be configured to be disposed in contact with an exterior surface of the bone and thus may be positioned at least substantially (or completely) exterior to the bone. Alternatively, the bone plate may be configured to be disposed at least partially interior to a bone, that is, apposed to (normally) interior bone surfaces when secured to the bone. The interior surfaces of the bone may be accessed during installation of the bone plate (such as by punching the bone plate through the exterior bone surface) and/or may be accessible due to a break, a cut, and/or the like.

The bone plates may be formed of any suitable material(s). The bone plates may be of a sturdy yet malleable construction. Generally, the bone plates should be stiffer and stronger than the section of bone spanned by the plates, yet flexible (e.g., springy) enough not to strain the bone significantly. Suitable materials for forming the bone plates may include metal, polymer, plastic, ceramic, composite, and/or the like. Suitable materials may include biocompatible materials. Exemplary biocompatible materials may include metals/metal alloys (for example, titanium or titanium alloys; alloys with cobalt, chromium, and/or molybdenum; stainless steel; etc.) and/or bioresorbable materials (such as polygalactic acid (PGA), polylactic acid (PLA), polycaprolactones, polydioxanones, copolymers thereof, etc.), among others. The materials may be specially selected and/or treated (e.g., by annealing) to facilitate tapping, for example, being softer than at least the cutting portion of the tap, and potentially being softer than regular bone plates (although still hard enough to perform the desired function).

The bone plates may be configured to reduce irritation to the bone and surrounding tissue. For example, the bone plates may be formed of a biocompatible material, as described above. In addition, the bone plates may have a low and/or feathered profile to reduce their protrusion into adjacent tissue and rounded, burr-free surfaces to reduce the effects of such protrusion.

The bone plates described herein may be sized and shaped to conform to particular portions of a bone (or bones). The plates may be generally elongate, with a length L, a width W, and a thickness T. Here, length L≧width W>thickness T. In use, the long axis of the bone plates (or of a plate portion) may be aligned with the long axis of the corresponding bone, and/or may extend obliquely and/or transversely relative to the bone's long axis. The length and/or width of the bone plates may be varied according to the intended use, for example, to match the plates with a preselected region of bone(s) and/or a particular injury to the bone. For example, the plates may be generally linear for use on the shaft of a long bone and/or may have a nonlinear shape, such as for use near an end of a bone and/or for transverse placement on the shaft, among others. In some examples, the plates may be configured to wrap at least partially around a bone, so that portions of each plate are disposed on distinct sides and/or generally opposing sides/surfaces of a bone. In some embodiments, the bone plates may be configured for use on both sides of the body/skeleton, such as when the bone plates are bilaterally symmetrical. In some embodiments, the bone plates may be asymmetrical and configured for use on either the left or the right side of the body/skeleton.

The bone plates may include inner (bone-facing) and outer (bone-opposing) surfaces. One or both of these surfaces may be contoured generally to follow an exterior surface of a target bone (or bones) for which a bone plate is intended, so that the bone plate maintains a low profile and fits onto the bone(s). For example, the inner surface of a plate may be generally complementary in contour to the bone surface. The outer surface of the plate also may correspond in contour to the bone surface and may be generally complementary to the inner surface of the plate. The bone plates may be partially and/or completely precontoured, at the time of manufacture, allowing practitioners to apply them to bone(s) with little or no additional bending at the time of application. Preshaping the plates allows the inner or bone-facing surface of the plate to follow and substantially match the three-dimensional contour of a bone, along the length of the plate and/or across the width of the plate. For example, the plates may include curved, bent, twisted, and/or tubular inner surfaces that are adapted to face bone and to guide the plates to set onto the bones, initially to enhance fixation and/or to template reduction of bone, and subsequently to increase stability, by grabbing and holding bone fragments. In some embodiments, the plates may be somewhat undercontoured along their long axes, for example, to accommodate soft tissue between a portion of the plate and the bone, or to allow additional custom contouring pre- or intraoperatively, among others. Alternatively, or in addition, the bone plates may be custom-contoured by practitioners before and/or during installation onto bone.

The thickness of the bone plates may be defined by the distance between the inner and outer surfaces of the plates. The thickness of the plates may vary between plates and/or within the plates, according to the intended use. For example, thinner plates may be configured for use on smaller bones and/or on bones or bone regions where soft tissue irritation is a greater concern. Thickness may be varied within the plates. For example, the plates may become thinner as they extend over protrusions (such as processes, condyles, tuberosities, and/or the like), reducing their profile and/or rigidity, among others. Alternatively, or in addition, the thickness may vary as an interior portion of the bone plate extends into bone, for example, becoming thinner to facilitate insertion of this interior portion or thicker to increase structural stability. The thickness of the plates also may be varied to facilitate use, for example, to make the plates thinner where they typically need to be deformed by bending and/or twisting the plates, such as at a junction (or bridge region) between plate portions. In this way, the plates may be thicker and thus stronger in regions where they may not need to be contoured, such as along the shaft of the bone.

The bone plates generally include a plurality of openings (apertures). The openings may be adapted to receive fasteners for securing the plates to bone. Alternatively, or in addition, one or more of the openings may be configured to alter the local rigidity of the plates, to permit the plates to be manipulated with a tool (such as an attachable handle), to facilitate blood flow to bone regions where the bone plates are installed, to promote healing, and/or the like. These openings may extend through the bone plates (between inner and outer surfaces) and/or may extend at least substantially parallel to the inner and/or outer surfaces of the bone plates.

The openings may have any suitable positions, sizes, and/or densities within each portion of a bone plate. The openings may be arrayed generally in a line along a portion of the plate, for example, centered across the width of the plate. Alternatively, the openings may be arranged nonlinearly, for example, disposed in an arcuate, staggered, or other two-dimensional (or three-dimensional) arrangement.

The openings may have any suitable shape and structure. Exemplary shapes may include circular, elongate (such as elliptical, rectangular, oval), etc. The openings may include counterbores. The counterbores may be configured, for example, to receive a head of a bone screw, to reduce or eliminate protrusion of the head above the outer surface of the plate. The openings may be threaded or nonthreaded, and each bone plate may include one or more threaded and/or nonthreaded openings. Threaded openings may be used to position at least a portion of a bone plate away from the bone, as described above, so that the periosteum, neurovascular bodies, and the like, may pass under the plate without being pinched or damaged.

Openings to be tapped (tappable apertures) may have any suitable shape and structure. Tappable apertures may be round, elliptical, oval, and/or the like. Tappable apertures may include a lip (a land) having a wall extending generally parallel to a thickness axis of the plate. The lip may be disposed adjacent the inner (bone-facing) surface of the bone plate (and spaced from the outer surface of the bone plate). Accordingly, with a circular tappable aperture, the lip or land may define a cylindrical region of the aperture to be tapped. Tappable apertures may include or lack a counterbore, generally disposed adjacent the outer (bone-opposing) surface of the bone plate (and spaced from the inner surface of the bone plate). The counterbore may have any suitable shape including frustoconical, radiused (such as a generally frustospherical), and/or a combination thereof, among others. In some examples, a concave radiused (such as frustospherical) counterbore may be preferred over a frustoconical counterbore, because a thread may be formed by removing less material from the bone plate during intraoperative tapping.

In some embodiments, the plates may include one or a plurality of elongate openings (for example, oval openings) extending axially, obliquely, and/or transversely within each bone plate. The elongate openings may be compression slots that include tapered counterbores to provide compression when heads of bone screws are advanced against the counterbores. Alternatively, or in addition, the elongate openings may be used to adjust the position of bone plates and/or plate portions relative to bone before the plates are fully secured to the bone. In some examples, some or all of the elongate openings may be configured to be tapped intraoperatively, as discussed above. In other examples, some or all of the elongate openings may not be configured to be tapped intraoperatively, whereas at least one or more circular openings in the bone plate may be configured to be tapped intraoperatively.

In some examples, the bone plates may include one or more projections. The projections may extend, for example, generally orthogonal from the inner surface of the bone plates toward bone. The projections may be sharp or blunt according to their intended use. For examples, sharp projections may be configured as prongs that penetrate bone to restrict movement of the bone plates. Prongs may be used in place of, or in addition to, bone fasteners, for one or more portions of each bone plate. Blunt (or sharp) projections, such as ridges or knobs, may be configured as spacing members that elevate the bone plates from the bone surface.

The bone plates may have at least one, and generally two or more, plate portions (or anchor portions) configured to be secured to different regions of a bone (or bones). Each plate portion may be structured for a specific region of a bone. For example, the bone plates may include a proximal plate portion for attachment to a more proximal region of a bone, and a distal plate portion for attachment to a more distal region of the same bone. Alternatively, or in addition, the bone plates may include an exterior plate portion configured to fit against an exterior surface region of bone adjacent a bone discontinuity, and/or an interior plate portion configured to be received in an interior (e.g., recessed, resected, and/or excavated) region of bone adjacent the bone discontinuity.

The plate portions of a bone plate may have any suitable connection. In some examples, the plate portions may be formed integrally, so that one piece of the bone plate includes the plate portions. Alternatively, plate portions may be formed as separate pieces. The separate pieces may be connected by any suitable connection and/or joint, including a fastener(s), welding, a hinge joint, a ball-in-socket joint, and/or the like. Further aspects of bone plates having adjustable joints are described in the following patent application, which is incorporated herein by reference: U.S. patent application Ser. No. 10/716,719, filed Nov. 19, 2003.

The plate portions of a bone plate may have any suitable relative disposition. The plate portions may be disposed such that they are substantially collinear and/or parallel, oblique, or substantially transverse to one another. The relative disposition may be fixed and/or adjustable. In some examples, the plate portions may be connected integrally by a deformable bridge region, so that the bone plate can be bent pre- or intraoperatively to adjust the relative disposition of the plate portions. Alternatively, the plate portions may be distinct pieces connected, for example, through an adjustable joint, as described above.

V. Guide Devices

The systems of the present teachings may include one or more guide devices. A guide device may include any structure, other than the bone plate or bone, that guides hole formation in bone (and/or in the bone plate), thread formation in the bone plate (and/or bone), and/or fastener placement.

The guide device may form a channel along which a fastener, a tap device, a reamer, and/or a drill may be guided. The channel may have any suitable structure, such as linear or nonlinear. The channel may be generally cylindrical or noncylindrical. The channel may be hollow (such as a tube with an axial bore) and/or may be solid (such as a guide wire).

The guide device may be held in position during its use by any suitable mechanism. For example, the guide device may be held manually, such as through a handle and/or other graspable portion. Alternatively, or in addition, the guide device may be held with an auxiliary device, such as a positioning jig, and/or it may be secured directly to the bone plate and/or bone, such as with a fastener(s), a clamp, and/or the like.

Figure 13:
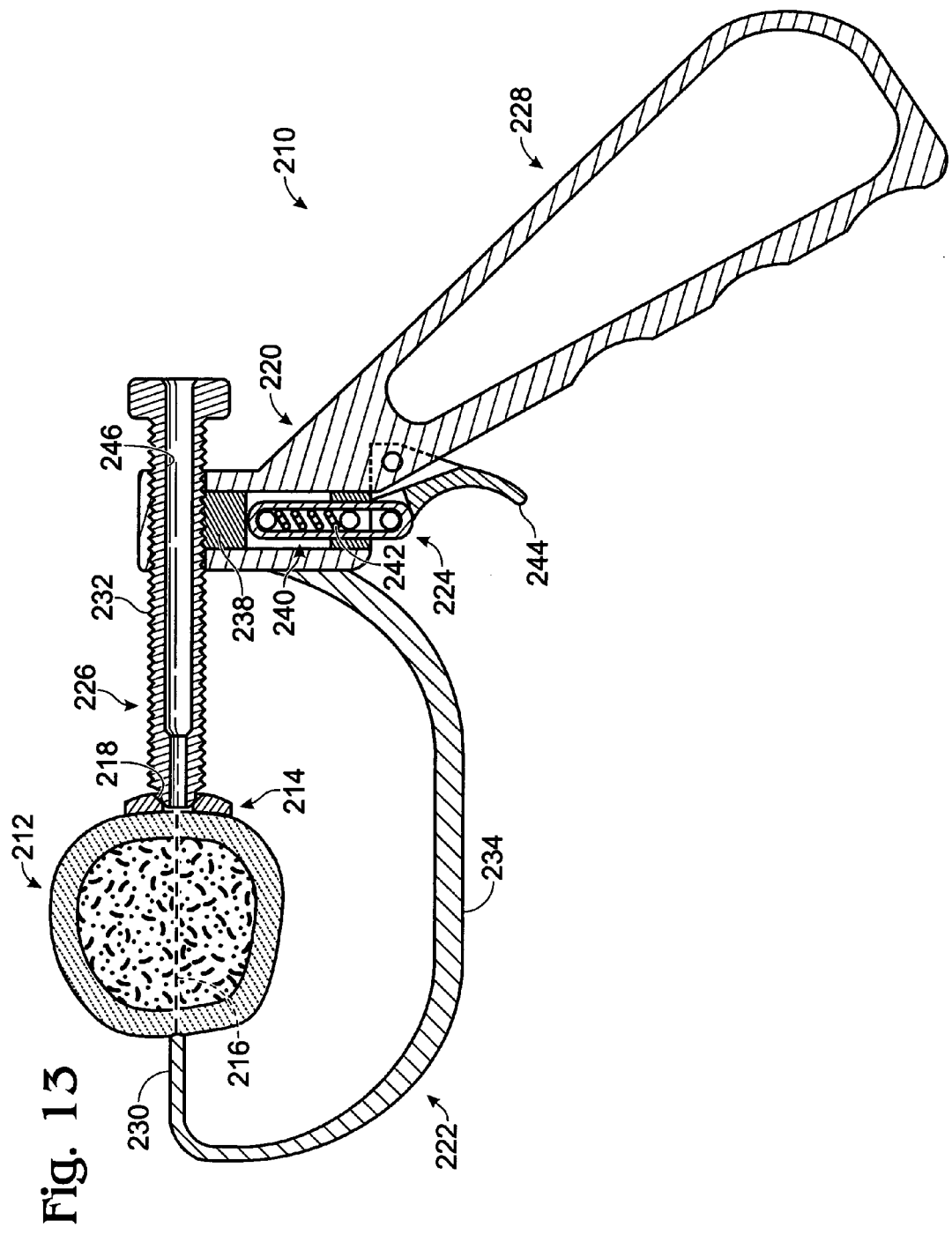
FIG. 13 is a sectional view of an exemplary guide device clamped to a bone and a bone plate and defining a path through an aperture of the bone plate and into the bone, in accordance with aspects of the present teachings.

FIG. 13 shows an exemplary guide device 210 clamped to a bone 212 and a bone plate 214. The guide device may define a path 216 through an aperture 218 of the bone plate and into the bone. The path may be defined between positions of opposing engagement of the guide device with bone and/or the bone plate. The guide device may include a frame 220 that holds or includes a clamp portion 222, a clamp release mechanism 224, a guide portion 226, and a handle portion 228.

The clamp portion 222 may be configured to apply a compressive force to the bone plate and the bone. The compressive force may restrict slippage of the clamp device and/or the bone plate. The clamp portion may include a pincer formed by opposing (first and second) pincer members 230, 232. First pincer member 230 may be included in an arm 234 extending from the frame 220 to an opposing surface of the bone. The first pincer member may indicate a location where a pilot hole, tap device, and/or fastener would exit the bone opposite the plate. Thus, the first pincer member may serve as an indicator that shows the linear extension from the guide portion, along path 216, through the bone. This may enable a surgeon to choose more precisely a suitable angle at which in to form a pilot hole, tap the bone plate, and/or place a fastener. Second pincer member 232 may be threadably coupled to the frame, so that rotation of the second pincer member adjusts the spacing between the pincer members, and thus how tightly the bone and bone plate are engaged.

The clamp release mechanism 224 may include a threaded block or retainer 238 biased into threaded engagement with the second pincer member 232. The retainer may be biased with a biasing mechanism 240 including a spring 242 or other biasing element. A switch, such as a lever or trigger 244, may be coupled to the biasing mechanism 240, and may be operable to release second pincer member 232 from engagement with retainer 238, to allow release and/or repositioning of the clamp portion.

Guide portion 226 may be formed at least partially by the second pincer member 232. The guide portion 226 may include an axial bore 246 sized to receive a drill, a tap device, and/or a fastener, among others.

VI. Kits

The systems of the present teachings may provide kits for tapping apertures intraoperatively. These kits may include (1) one or more tap devices, (2) one or more bone plates, (3) fasteners such as bone screws, (4) a guide device, and/or (5) instructions for their use, among others.

The kits may include one or more tap devices. Tap devices included in a kit may be of various sizes, including tap devices with different lengths, diameters, thread pitches, and/or thread depths, to be used in conjunction with various bone plates and/or fasteners for fixation of various types of fractures. For example, the tap devices may have tap portions of various lengths to accommodate bone plates of different thicknesses, and they may have tap portions of various diameters to accommodate bone plate apertures of different sizes. The tap devices in a kit also may have tap portions of various thread patterns, to tap apertures for engaging various sizes/types of bone screws. The tap devices also may have tip portions of different lengths and/or diameters, to follow and/or form pilot holes of different depths and/or diameters, for example, according to the length and/or diameter of bone screws to be placed into the tapped apertures. A kit may include a plurality of interchangeable tap portions and/or a plurality of interchangeable tip portions, to accommodate various combinations of bone plate thickness, aperture diameter, thread pattern, pilot hole diameter, and/or pilot hole depth, among others.

Bone plates provided in kits (or selected otherwise) may be sized and/or shaped to conform to particular regions of bone, or to different portions of the same region of bone, among others. In particular, the plates may be preshaped (preformed) to fit an average target anatomy, such as a population-averaged shape of a particular anatomical region. The average anatomy may be a human (or other animal) anatomy averaged over any suitable set, such as, for example, adults, adult males, adult females, people that fall within a particular size range, children of a given age, and so on. The bone plates may include one or more apertures, such as one or more circular and/or oval apertures. In some examples, the kits may include at least one bone plate having a circular aperture corresponding generally in diameter to the root-to-root diameter of a tap portion of a tap device in the kits.

Fasteners, such as bone screws, provided in kits (or selected otherwise) may be sized and/or shaped in correspondence with one or more tap devices included in the kits. For example, the kits may include bone screws with a head configured to be threadably engaged with a thread formed by a tap device of the kit, and/or with a shank configured to be threadably engaged with bone surrounding a pilot hole formed and/or followed by the tap device. The kits also may include one or more additional fasteners configured to be placed into bone from nonthreaded apertures of the bone plates.

The kits also may include additional tools and/or consumable surgical supplies that may be required for carrying out the connective tissue repair, substantially as described above, such as additional clamps and/or other surgical tools that may facilitate grasping and/or positioning the connective tissue that is being repaired.

The kits may be constructed or assembled for single and/or multiple use. For example, the kits, or components thereof, may be configured, in some embodiments, for a single use, such as tapping a single aperture, a single plate, or a set of plates during a single surgical procedure. These embodiments optionally may be prepackaged in a sterile wrapper. Thus, as needed, components of the kit could be removed from the sterile wrapper, used to tap and install one or more plates, and then discarded. Alternatively, the kits, or components thereof, may be configured, in other embodiments, for effecting multiple repairs, during the same or different surgical procedures. In these cases, reusable components may be configured to reduce contamination (e.g., via smooth surfaces) and/or to facilitate sterilization, such as by washing and autoclaving (e.g., through choice of material, such as metal).

VII. EXAMPLES

The following examples describe selected aspects and embodiments of the present teachings, as a series of ordered paragraphs. These examples are included for illustration and are not intended to limit or define the entire scope of the invention.

1. A kit for internally fixing a discontinuity in a bone, comprising: a drill tap, including (1) a tapping portion including a plurality of external threads configured to intraoperatively form internal threads in the aperture of a bone plate; and (2) a guidance tip, attached to the tapping portion, configured to follow and/or form a pilot hole in a bone.

2. The kit of paragraph 1, wherein the guidance tip is detachable from the tapping portion.

3. The kit of paragraph 1, wherein the drill tap further comprises a shaft portion adapted to engage with a turning mechanism.

4. The kit of paragraph 1, wherein the drill tap further comprises a tapered portion, disposed between the tapping portion and the guidance tip, for forming a tapered region of the pilot hole.

5. The kit of paragraph 1, further comprising:

a clamp guide, including a bone clamp portion for holding the bone plate to the bone; and a drill guide portion configured to provide alignment for the drill tap.

6. The kit of paragraph 5, wherein the clamp guide further comprises an indicator configured to indicate a linear extension of the drill tap through the bone.

7. The kit of paragraph 5, further comprising a bone plate having at least one threadable aperture.

8. The kit of paragraph 1, further comprising a bone plate having at least one threadable aperture.

9. A method of internally fixing a discontinuity in a bone, comprising: (1) selecting a bone plate having at least one threadable aperture; (2) positioning the plate on a surface of the fractured bone; (3) threading intraoperatively at least one of the threadable apertures; and (4) attaching the plate to the bone by inserting a threaded fastener into one or more of the intraoperatively threaded apertures.

10. The method of paragraph 9, the threaded fastener being a bone screw, wherein threads of the bone screw engage threads of the aperture.

11. The method of paragraph 10, further comprising drilling a pilot hole in the bone for engaging a shaft portion of the bone screw.

12. The method of paragraph 11, wherein the steps of drilling a pilot hole and intraoperatively threading at least one of the threadable apertures are performed sequentially.

13. The method of paragraph 11, wherein the steps of drilling a pilot hole and intraoperatively threading at least one of the threadable apertures are performed at least partially simultaneously.

14. The method of paragraph 13, wherein the steps of drilling a pilot hole and intraoperatively threading at least one of the threadable apertures are performed by a drill tap comprising: (1) a tapping portion including a plurality of external threads configured to form internal threads in the aperture of a bone plate; and (2) a guidance tip, rigidly attached to the tapping portion, configured to follow and/or form a pilot hole in a bone.

15. The method of paragraph 9, further comprising clamping the bone plate to the bone, prior to the step of intraoperatively threading.

16. The method of paragraph 15, further comprising selecting an angle for threading the threadable aperture.

17. The method of paragraph 16, further comprising aligning a drill tap at the selected angle with a clamp guide.

18. The method of paragraph 9, wherein the step of intraoperatively threading at least one of the threadable apertures comprises: (1) tapping the at least one of the threadable apertures to create threads using a drill tap; and (2) removing the drill tap from the at least one of the threadable apertures, so that the aperture is accessible to a fastener.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of tapping a bone plate intraoperatively, comprising:
   selecting a bone plate having an aperture;
   placing the bone plate on a bone;
   forming a thread in the aperture using a tap device with the bone plate disposed on the bone;
   forming a hole in the bone, the hole being in alignment with the aperture;
   widening the hole adjacent the aperture to create a counterbore in the bone; and
   advancing a fastener into threaded engagement with the thread after removal of the tap device from the aperture.

2. The method of claim 1, wherein the step of placing includes a step of attaching the bone plate to the bone.

3. The method of claim 2, the aperture being a first aperture, wherein the step of attaching includes a step of inserting a fastener through a second aperture and into the bone.

4. The method of claim 1, wherein the step of forming a hole also forms a thread in the bone.

5. The method of claim 1, wherein the step of forming a hole is performed at least substantially before the step of forming a thread.

6. The method of claim 5, wherein the step of forming a thread is performed with a tap device having a tap portion and a tip portion, and wherein the step of forming a thread includes a step of inserting the tip portion into the hole so that the tap portion is guided to the aperture.

7. The method of claim 1, further comprising a step of selecting an angle for the step of forming a thread.

8. The method of claim 7, wherein the step of selecting an angle includes a step of disposing a guide device at least substantially at the angle.

9. The method of claim 7, wherein the step of forming a hole in the bone includes a step of forming a hole at least substantially at the angle.

10. The method of claim 1, wherein the step of selecting a bone plate includes selecting a bone plate formed at least substantially of metal.

11. The method of claim 10, wherein the step of selecting a bone plate includes selecting a bone plate formed at least substantially of titanium.

12. The method of claim 1, wherein the step of forming a thread includes a step of cutting the thread.

13. The method of claim 1, wherein the counterbore is defined in the bone by a wall, and wherein the step of advancing includes a step of disposing the fastener in threaded engagement with the wall.

14. The method of claim 13, wherein the fastener has a head with a threaded region, and wherein the step of advancing a fastener includes a step of advancing the threaded region into threaded engagement with the thread in the aperture and with the wall.

15. The method of claim 1, wherein the step of widening the hole includes a step of creating a counterbore having a thread for engagement with the fastener.

16. The method of claim 1, wherein the step of advancing a fastener includes a step of tapping the counterbore.

17. The method of claim 1, wherein the bone plate has a thickness, and wherein the step of advancing is performed with a fastener having a head that is longer than the thickness of the bone plate.

18. The method claim 1, wherein the step of widening is performed at least partially during the step of forming a thread.

* * * * *